United States Patent
Veronesi et al.

(10) Patent No.: US 10,342,779 B2
(45) Date of Patent: Jul. 9, 2019

(54) ANHYDROUS LIQUID MELATONIN COMPOSITION

(71) Applicant: Therapicon S.R.L., Milan (IT)

(72) Inventors: Paolo Alberto Veronesi, Milan (IT); Emanuela Peschechera, Milan (IT); Susanna Veronesi, Milan (IT)

(73) Assignee: WORPHMED SRL, Milan (IT)

( * ) Notice: Subject to any disclaimer, the term of this patent is extended or adjusted under 35 U.S.C. 154(b) by 0 days.

(21) Appl. No.: 15/514,402

(22) PCT Filed: Oct. 12, 2015

(86) PCT No.: PCT/EP2015/073552
§ 371 (c)(1),
(2) Date: Mar. 24, 2017

(87) PCT Pub. No.: WO2016/058985
PCT Pub. Date: Apr. 21, 2016

(65) Prior Publication Data
US 2017/0239217 A1    Aug. 24, 2017

(30) Foreign Application Priority Data
Oct. 13, 2014  (IT) .............................. MI2014A1781

(51) Int. Cl.
| | |
|---|---|
| *A61K 9/00* | (2006.01) |
| *A61K 9/08* | (2006.01) |
| *A23L 33/10* | (2016.01) |
| *A61K 47/10* | (2017.01) |
| *A61K 47/14* | (2017.01) |
| *A61P 31/12* | (2006.01) |
| *A61K 31/4045* | (2006.01) |

(52) U.S. Cl.
CPC .......... *A61K 31/4045* (2013.01); *A23L 33/10* (2016.08); *A61K 9/006* (2013.01); *A61K 9/0019* (2013.01); *A61K 9/0053* (2013.01); *A61K 9/08* (2013.01); *A61K 47/10* (2013.01); *A61K 47/14* (2013.01); *A61P 31/12* (2018.01); *A23V 2002/00* (2013.01)

(58) Field of Classification Search
CPC . A23L 33/10; A23V 2002/00; A61K 31/4045; A61K 47/10; A61K 47/14; A61K 9/0019; A61K 9/0053; A61K 9/006; A61K 9/08
USPC ................................... 514/1.1, 419
See application file for complete search history.

(56) References Cited

U.S. PATENT DOCUMENTS

| | | | | |
|---|---|---|---|---|
| 5,498,423 A * | 3/1996 | Zisapel | ................ | A61K 9/0027 424/462 |
| 5,500,225 A * | 3/1996 | Laudon | ................ | A61K 9/0027 424/464 |
| 5,939,084 A | 8/1999 | Simon et al. | | |
| 9,468,626 B2 * | 10/2016 | Raschini | ............ | A61K 31/4045 |
| 2008/0051351 A1 * | 2/2008 | Ghisalberti | .......... | A61K 8/4953 514/25 |
| 2014/0308357 A1 * | 10/2014 | Maggi | .................. | A61K 9/0019 424/489 |

FOREIGN PATENT DOCUMENTS

| | | | |
|---|---|---|---|
| CN | 102451179 A | 5/2012 | |
| EP | 1174134 A1 | 1/2002 | |
| WO | WO-2009024360 A1 * | 2/2009 | ............... A61K 8/34 |
| WO | 2012156565 A1 | 11/2012 | |
| WO | 2013068565 A2 | 5/2013 | |

OTHER PUBLICATIONS

Editors: Rowe et al., "Handbook of Pharmaceutical Excipients", Sixth Edition, 2009, pp. 17-19. (Year: 2009).*
Johns et al., "An intravenous injection of melatonin: formulation, stability, pharmacokinetics and pharmacodynamics", 2012, J. Asian Association of Schools of Pharmacy (JAASP; ISSN: 2286-6493), 1(1), pp. 32-43. (Year: 2012).*
Lee et al., "Solubility and Stability of Melatonin in Propylene glycol and 2-Hydroxypropyl-(beta)-cyclodextrin Vehicles", 1997, Arch. Pharm.Res., 20(6), pp. 560-565. (Year: 1997).*
Kolliphor™ HS 15 (Macrogol 15 Hydroxystearate Ph. Eur.; Polyoxyl 15 Hydroxystearate USP) BASF brochure, Mar. 2012. (Year: 2012).*
Lane, E. et al., Pharmacokinetics of Melatonin in Man, First Pass Hepatic Metabolism, Journal of Clinical Endocrinology and Metabolism, 1985, 61, pp. 1214-1216.
Bagci, S. et al., Melatonin Status in Pediatric Intensive Care Patients with Sepsis, Pediatr Crit Care Med, 2012, 13, pp. e120-e123.
Moroni, B. et al., Pharmacokinetics of Orally Adminstered Melatonin in Critically Ill Patients, 30th International Syposium on Intensive Care and Emergency Medicine, Brussels, Belgium, Mar. 9-12, 2010.
Alan, K. et al., Prognostic Value of Melatonin in Patients with Sepsis: A Comparison of Survivors and Nonsurvivors, 0th International Syposium on Intensive Care and Emergency Medicine, Brussels, Belgium, Mar. 9-12, 2010.

(Continued)

Primary Examiner — My-Chau T. Tran
(74) Attorney, Agent, or Firm — Standley Law Group LLP

(57) ABSTRACT

The present invention relates to a concentrated melatonin solution, wherein melatonin is present in a quantity of 10.0% or higher in a substantially water-free carrier mixture of ethanol and a polyethoxylated derivative. The concentrated solution, free of preserving agents, is suitable to prepare injectable sterile compositions for parenteral administration, or formulations for topical or oral administration. The invention also encompasses a method for the preparation of the concentrated solution, as well as the possible benefits of the intravenous infusion of high levels of melatonin as adjuvant therapy in Ebola or Dengue hemorrhagic fever (DHF) or as an anti-oxidant/anti-aging treatment.

22 Claims, 2 Drawing Sheets

(56) References Cited

OTHER PUBLICATIONS

Figure 1:
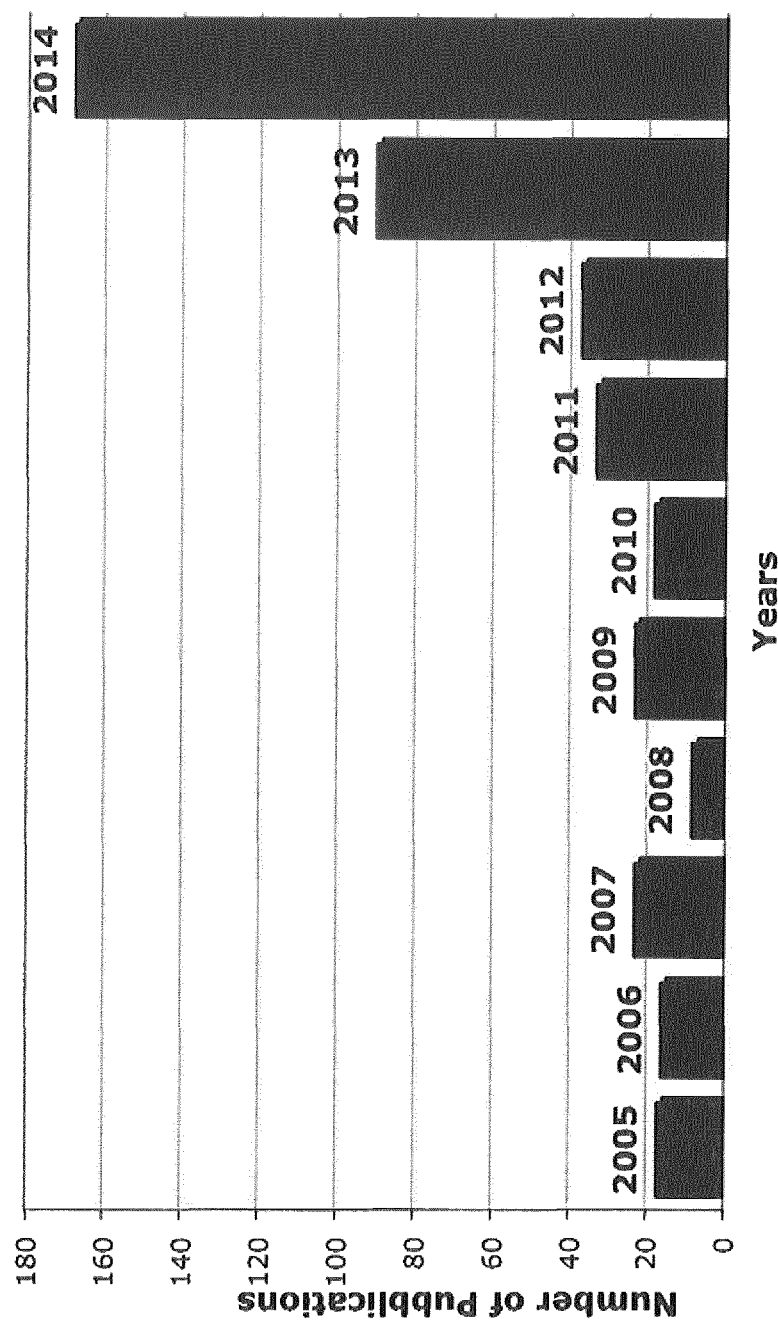

Srinivasan, V. et al., Melatonin in Septic Shock: Some Recent Concepts, Journal of Critical Care, 2010, 25, pp. 656. e1-656.e6.
Galley, H. et al., Melatonin as a Potential Therapy for Sepsis: A Phase I Dose Escalation Study and an Ex Vivo Whole Blood Model Under Conditions of Sepsis, J. Pineal Res., 2014, 56, pp. 427-438.
Shinozuka, K. et al., Melatonin-Based Therapeutics for Neuroprotection in Stroke, International Journal of Moleculer Sciences, 2013, 14, pp. 8924-8947.
Manev, H. et al., Increased Brain Damage After Stroke or Excitotoxic Seizures in Melatonin-Deficient Rats, The FASEB Journal, 1996, 10, pp. 1546-1551.
Kilic, E. et al., Pinealectomy Aggravates and Melatonin Adminstration Attenuates Brain Damange in Focal Ischemia, Journal of Cerebral Blood Flow and Metabolism, 1999, 19, pp. 511-516.
Pei, Z. et al., Adminstration of Melatonin After Onset of Ischemia Reduces the Volume of Cerebral Infarction in a Rat Middle Cerebral Artery Occlusion Stroke Model, Journal of the American Heart Association, 2003, 34, pp. 770-775.
Sinha, K. et al., Effect of Melatonin on Ischemia Reperfusion Injury Induced by Middle Cerebral Artery Occlusion in Rats, European Journal of Pharmacology, 2001, 428, pp. 185-192.
Lee, E-Jian et al., Melatonin Attenuates Gray and White Matter Damage in a Mouse Model of Transient Focal Cerebral Ischemia, J. Pineal Res., 2005, 38, pp. 42-52.
Lee, Ming-Yang et al., Intravenous Adminstration of Melatonin Reduces the Intracerebral Cellular Inflammatory Response Following Transient Focal Cerebral Ischemia in Rats, J. Pineal Res., 2007, 42, pp. 297-309.
Kondoh, T. et al., Melatonin Reduces Cerebral Edema Formation Caused by Transient Forebrain Ischemia in Rats, Life Sciences, 2002, 72, pp. 583-590.
Chen, Tsung-Ying et al., Melatonin Attenuates the Postischemic Increase in Blood-Brain Barrier Permiability and Decreases Hemorrhagic Transformation of Tissue-Plasminogen Activator Therapy Following Ischemic Stroke in Mice, J. Pineal Res., 2006, 40, pp. 242-250.
Kilic, E. et al., Delayed Melatonin Adminstration Promotes Neuronal Survival, Neurogenesis an Motor Recovery, and Attenuates Hyperactivity and Anxiety After Mild Focal Cerebral Ischemia in Mice, J. Pineal Res., 2008, 45, pp. 142-148.
Brzezinksi, A., Melatonin in Humans, The New England Journal of Medicine, 1997, 336, pp. 186-195.
Pei, Z. et al., Pre-Treatment with Melatonin Reduces Volume of Cerebral Infarction in a Permanent Middle Cerebral Artery Occlusion Stroke Model in the Rat, Neuroscience Letters, 2002, 318, pp. 141-144.
Pei, Z. et al., Pretreatment with Melatonin Reduces Volume of Cerebral Infarction in a Rat Middle Cerebral Artery Occlusion Stroke Model, J. Pineal Res., 2002, 32, pp. 168-172.
Borlongan, C. et al., Glial Cell Survival is Enhanced During Melatonin-Induced Neuroprotection Against Cerebral Ischemia, The FASEB Journal, 2000, 14, pp. 1307-1317.
Reiter, R. et al., When Melatonin Gets on Your Nerves: Its Beneficial Actions in Experimental Models of Stroke, Exp Biol Med, 2005, 230, pp. 104-117.
Generali, J. et al., Melatonin: Delirium (Postsurgical), Hosp Pharm, 2013, 48, pp. 378-379.
Wilhelmsen, M. et al., Analgesic Effects of Melatonin: a Review of Current Evidence from Experimental and Clinical Studies, J. Pineal Res., 2011, 51, pp. 270-277.
Azevedo de Zanette, S. et al., Melatonin Analgesia is Assocaited with Improvement of the Descending Endogenous Pain-Modulating System in Fibromyalgia: A Phase II, Randomized, Double-Dummy, Controlled Trial, BMC Pharmacology and Toxicology, 2014, 15, pp. 1-14.
Kurdi, M. et al., the Role of Melatonin in Anaesthesia and Critical Care, Indian Journal of Anaesthesia, 2013, 57, pp. 137-144.
Holley, J. et al., A Comparison of Reported Sleep Disorders in Patients on Chronic Hemodialysis and Continuous Peritoneal Dialysis, Am J Kidney Dis, 1992, 19, pp. 156-161.
Walker, S. et al., Sleep Complaints are Common in a Dialysis Unit, American Journal of Kidney Diseases, 1995, 26, pp. 751-756.
Masoumi, M. et al., Sleep Quality in Patients on Maintenance Hemodialysis and Peritoneal Dialysis, Int J Prev Med, 2013, 4, pp. 165-172.
Kock, B. et al., Effects of Nocturnal Hemodialysis on Melatonin Rhythm and Sleep-Wake Behavior: An Uncontrolled Trial, American Journal of Kidney Diseases, 2009, 53, pp. 658-664.
Russcher, M. et al., The Role of Melatonin Treatment in Chronic Kidney Disease, Frontiers in Bioscience, 2012, 17, pp. 644-2656.
Sharma, U., On Dialysis, Sleep and Melatonin, Indian J Nephrol., 2013, 23, pp. 269-270.
Aperis, G. et al., The Role of Melatonin in Patients with Chronic Kidney Disease Undergoing Haemodialysis, Journal of Renal Care, 2012, 99. 86-92.
Edalat-Nejad, M. et al., Melatonin Improves Sleep Quality in Hemodialysis Patients, Indian J Nephrol., 2013, 23, pp. 264-269.
Jaworek, J. et al., Melatonin Influences Pancreatic Cancerogenesis, Histol Histopathol, 2014, 29, pp. 423-431.
Katkar, G. et al., Melatonin Alleviates Echis Carinatus Venom-Induced Toxicities by Modulating Inflammatory Mediators and Oxidative Stress, J. Pineal Res., 2014, 56, pp. 295-312.
Shida, C. et al., High Melatonin Solubility in Aqueous Medium, J. Pineal Res., 1994, 16, pp. 198-201.
Kandimalla, K. et al., Optimization of a Vehicle Mixture for the Transdermal Delivery of Melatonin Using Artificial Neural Networks and Response Surface Method, Journal of Controlled Release, 1999, 61, pp. 71-82.
Andrisano, V. et al., Photostability of Drugs: Photodegradation of Melatonin and its Determination in Commercial Formulations, Journal of Pharmaceutical and Biomedical Analysis, 2000, 23, pp. 15-23.
Daya, S. et al., The Effect of Variations in pH and Temperature on Stability of Melatonin in Aqueous Solution, J. Pineal Res., 2001, 31, pp. 155-158.
Dayal, P. et al., Development of Bioadhesive Dosage Forms of Melatonin with Different Polymers: Release Studies and Characterization of the Formulations by DSC, AAPS Pharm Sci, 2003, 5, T3017.
Lee, B. et al., Solubility and Stability of Melatonin in Propylene Glycol and 2-Hydroxyproply-B-cyclodextrin Vehicles, Arch. Pharm. Res., 1997, 20, pp. 560-565.
Lee, B. et al., Percutaneous Absoption and Model Membrane Variations of Melatonin in Aqueous-based Propylene Glycol and 2-Hydroxypropyl-β-cyclodextrin Vehicles, Arch. Pharm. Res., 1998, 21, pp. 503-507.
Cavallo, A. et al., Stability of Melatonin in Aqueous Solution, J. Pineal Res., 1995, 18, pp. 90-92.
Cheung, R. et al., Preclinical Evaluation of Pharmacokinetics and Safety of Melatonin in Propylene Glycol for Intravenous Administration, J. Pineal Res., 2006, 41, pp. 337-343.
Malow, B. et al., Melatonin for Sleep in Children with Autism: A Controlled Trial Examining Dose, Tolerability, and Outcomes, J. Autism Dev Disord, 2012, 42, pp. 1729-1737.
Humphreys, J. et al., Sleep Patterns in Children with Autistic Spectrum Disorders: A Prospective Cohort Study, Arc Dis Child, 2014, 99, pp. 114-118.
Yeleswaram, K. et al., Pharmacokinetics and Oral Bioavailability of Exogenous Melatonin in Preclinical Animal Models and Clinical Implications, Journal of Pineal Research, 1997, 22, pp. 45-51.
Waldhauser, F. et al., Bioavailability of Oral Melatonin in Humans, Neuroendocrinology, 1984, 39, pp. 307-313.
Shirakawa, S. et al., Time Course of Saliva and Serum Melatonin Levels After Ingestion of Melatonin, Psychiatry and Clinical Neurosciences, Japanese Society of Sleep Research, 1998, pp. 266-267.
Fourtillan, J. et al., Bioavailability of Melatonin in Humans After Day-Time Administration of D7 Melatonin, Biopharmaceutics & Drug Disposition, 2000, 21, pp. 15-22.

(56) References Cited

OTHER PUBLICATIONS

Vakkuri, O. et al., Oral Administration and Distribution of Melatonin in Human Serum, Saliva and Urine, Melatonin After Oral Administration, 1985, 37, pp. 489-495.
Demuro, R. et al., The Absolute Bioavailability of Oral Melatonin, Alternative and Herbal Medicine, J Clin Pharmacol, 2000, 40, pp. 781-784.
Kopin, I. et al, The Fate of Melatonin in Animals, J. Biol. Chem., 1961, 236, pp. 3072-3075.
Vitte, P. et al., Plasma, Cerebrospinal Fluid, and Brain Distribution of 14C-Melatonin in Rat: A BioChemical and Autoradiographic Study, J Pineal Res., 1988, 5, pp. 437-453.
Mallo, C. et al., Pharmacokinetics of Melatonin in Man After Intravenous Infusion and Bolus Injection, Eur J Clin Pharmacol, 1990, 38, pp. 297-301.
Le Bars, D. et al., PET and Plasma Pharmacokinetic Studies After Bolus Intraveous Administration of [11C] Melatonin in Humans, Int J Rad Appl Instrum B, 1991, 18(3), pp. 357-362.
Facciolá, G. et al., Cytochrome P450 Isoforms Involved in Melatonin Metabolism in Human Liver Microsomes, Eur J Clin Pharmacol, 2001, 56, pp. 881-888.
Ma, X. et al., Metabolism of Melatonin by Human Cytochromes P450, Drug Metabolism and Disposition, 2005, 33, pp. 489-494.
Reiter, R. et al., Pharmacological Utility of Melatonin in Reducing Oxidative Cellular and Molecular Damage, Pol J Pharmacol, 2004, 56, pp. 159-170.
Vijayalaxmi, C. et al., Melatonin: From Basic Research to Cancer Treatment Clinics, J Clin Oncol, 2002, 20, pp. 2575-2601.
Korkmaz, A. et al., Melatonin: An Established Antioxidant Worthy of Use in Clinical Trials, Mol Med, 2009, 15, pp. 43-50.
Bonnefont-Rousselot, D. et al., Melatonin: Action as Antioxidant and Potential Applications in Human Disease and Aging, Toxicology, 2010, 278, pp. 55-67.
Medgal, S. et al., Night Work and Breast Cancer Risk: A Systematic Review and Meta-Analysis, European Journal of Cancer, 2005, 41, pp. 2023-2032.
Wetterberg, L., Melatonin and Clinical Application, Reprod. Nutr. Dev., 1999, 39, pp. 367-382.
Karamitri, A. et al., Minireview: Toward the Establishment of a Link Between Melatonin and Glucose Homeostasis: Association of Melatonin MT2 Receptor Variants with Type 2 Diabetes, Mol Endocrinol, 2013, 27, pp. 1217-1233.
Glaser, S. et al., Melatonin Regulation of Biliary Functions, Hepatobiliary Surg Nutr, 2014, 3, pp. 35-43.
Reiter, R. et al., Melatonin and Stable Circadian Rhythms Optimize Maternal, Placental and Fetal Physiology, Human Reproduction Update, 2014, 20, pp. 293-307.
Tordjman, S. et al., Advances in the Research of Melatonin in Autism Spectrum Disorders: Literature Review and New Perspectives, Int. J. Mol. Sci., 2013, 14, pp. 20508-20542.
Lin, L. et al., Melatonin in Alzheimer's Disease, Int. J. Mol. Sci., 2013, 14, pp. 14575-14593.
Wade, A. et al., Add-on Prolonged-Release Melatonin for Cognitive Function and Sleep in Mild to Moderate Alzheimer's Disease: a 6-Month, Randomized, Placebo-Controlled, Multicenter Trial.
Coto-Montes, A. et al., Role of Melatonin in the Regulation Autophagy and Mitophagy: a Review, Molecular and Cellular Endocrinology, 2012, pp. 1-12.
Suzuki, K. et al., Sleep Disturbances Associated with Parkinson's Disease, Parkinson's Disease, 2011, pp. 1-10.
Dowling, G. et al., Melatonin for Sleep Disturbances in Parkinson's Disease, Sleep Medicine, 2005, 6, pp. 459-466.
Srinivasan, V. et al., Therapeutic Potential of Melatonin and its Analogs in Parkinson's Disease: Focus on Sleep and Neuroprotection, Ther Adv Neurol Disord, 2011, 4, pp. 297-317.
Sterniczuk, R. et al., Sleep Disturbance in Older ICU Patients, Clinical Interventions on Aging, 2014, 9, pp. 969-977.
Adamczyk-Sowa, M. et al., Melatonin Acts as Antioxidant and Improves Sleep in MS Patients, Neurochem Res, 2014, 39, pp. 1585-1593.
Kinnucan, J. et al., Sleep and Infammatory Bowel Disease: Exploring the Relationship Between Sleep Disturbances and Inflammation, Gastroenterol Hepatol, 2013, 9, pp. 718-727.
Gitto, E. et al., Effects of Melatonin Treatment in Septic Newborns, Pediatric Research, 2011, 50, pp. 756-760.
Sahib, A. et al., Effect of Antioxidants on the Incidence of Wound Infection in Burn Patients, Annals of Burns and Fire Disasters, 2010, XXIII, pp. 199-205.
Dominguez-Rodriguez, A. et al., A Unicenter, Randomized, Double-Blind, Parallel-Group, Placebo-Controlled Study of Melatonin as an Adjunct in Patients With Acute MyocaRdial Infarction Undergoing Primary Angioplasty The Melatonin Adjunct in the Acute MyocaRdial Infarction Treated with Angioplasty (MARIA)Trial: Study Design and Rationale, Contemporary Clinical Trials, 2007, 28, pp. 532-539.
Caumo, W. et al., Preoperative Anxiolytic Effect of Melatonin and Clonidine on Postoperative Pain and Morphine Consumption in Patients Undergoing Abdominal Hysterectomy: A Double-Blind, Randomized, Placebo-Controlled Study, The Journal of Pain, 2009, vol. 10, pp. 100-108.
Borazan, H. et al., Effects of Preoperative Oral Melatonin Medication on Postoperative Analgesia, Sleep Quality, and Sedation in Patients Undergoing Elective Prostatectomy: A Randomized Clinical Trial, J Anesth, 2010, 24, pp. 155-160.
Gitto, E. et al., Melatonin Reduces Oxidative Stress in Surgical Neonates, Journal of Pediatric Surgery, 2004, 39, pp. 184-189.
Jarratt, J., Perioperative Melatonin Use, Anaesth Intensive Care, 2011, 39, pp. 171-181.
Maitra, S. et al., Melatonin in Perioperative Medicine: Current Perspecitve, Saudi J Anaesth, 2013, 7, pp. 315-321.
Wang, Y. et al., The Efficacy and Safety of Melatonin in Concurrent Chemotherapy or Radiotherapy for Solid Tumors: A Meta-Analysis of Randomized Controlled Trials, Cancer Chemother Pharmacol, 2012, 69, pp. 1213-1220.
Seeley, E. et al., Inflection Points in Sepsis Biology: From Local Defense to Systemic Organ Injury, Am J Physiol Lung Cell Mol Physiol, 2012, 303, pp. L355-L363.
Ghielmini, M. et al., Double-Blind Randomized Study on the Myeloprotective Effect of Melatonin in Combination with Carboplatin and Etoposide in Advanced Lung Cancer, British Journal of Cancer, 1999, 80, pp. 1058-1061.
Bennukul, K. et al., Melatonin Attenuates Cisplatin-Induced HepG2 Cell Death via the Regulation of mTOR and ERCC1 Expressions, World Journal of Hepatology, 2014, 6, pp. 230-242.
Martin, V. et al., Melatonin-Induced Methylation of the ABCG2/BCRP Promoter as a Novel Mechanism to Overcome Multidrug Resistance in Brain Tumor Stem Cells, British Journal of Cancer, 2013, 108, pp. 2005-2012.
Carrillo-Vico, A. et al., Melatonin: Buffering the Immune System, Int. J. Mol. Sci., 2013, 14, pp. 8638-8683.
Aversa, S. et al., Potential Utility of Melatonin as an Antioxidant During Pregnancy and in the Perinatal Period, The Journal of Maternal-Fetal & Neonatal Medicine, 2012, 25, pp. 207-221.
Ismail, S. et al., Melatonin Provides Anxiolysis, Enhances Analgesia, Decreases Intraocular Pressure, and Promotes Better Operating Condistions During Cataract Surgery Under Topical Anesthesia, International Anesthesia Research Society, 2009, 108, pp. 1146-1151.
Berk, L. et al., A Randomized Phase II Trial of High Dose Melatonin and Radiation Therapy for RPA Class 2 Patients with Brain Metastases (RTOG 0119), Int J Radiat Oncol Biol Phys, 2007, 68, pp. 852-857.
Gitto, E. et al., Protective Role of Melatonin in Neonatal Diseases, Oxidative Medicine and Cellular Longevity, Oxidative Medicine and Cellular Longevity, 2013, pp. 1-6.
Alonso-Alconada, D. et al., Neuroprotective Effect of Melatonin: A Novel Therapy Against Perinatal Hypoxia-Ischemia, Int. J. Mol. Sci., 2013, 14, pp. 9379-9395.

* cited by examiner

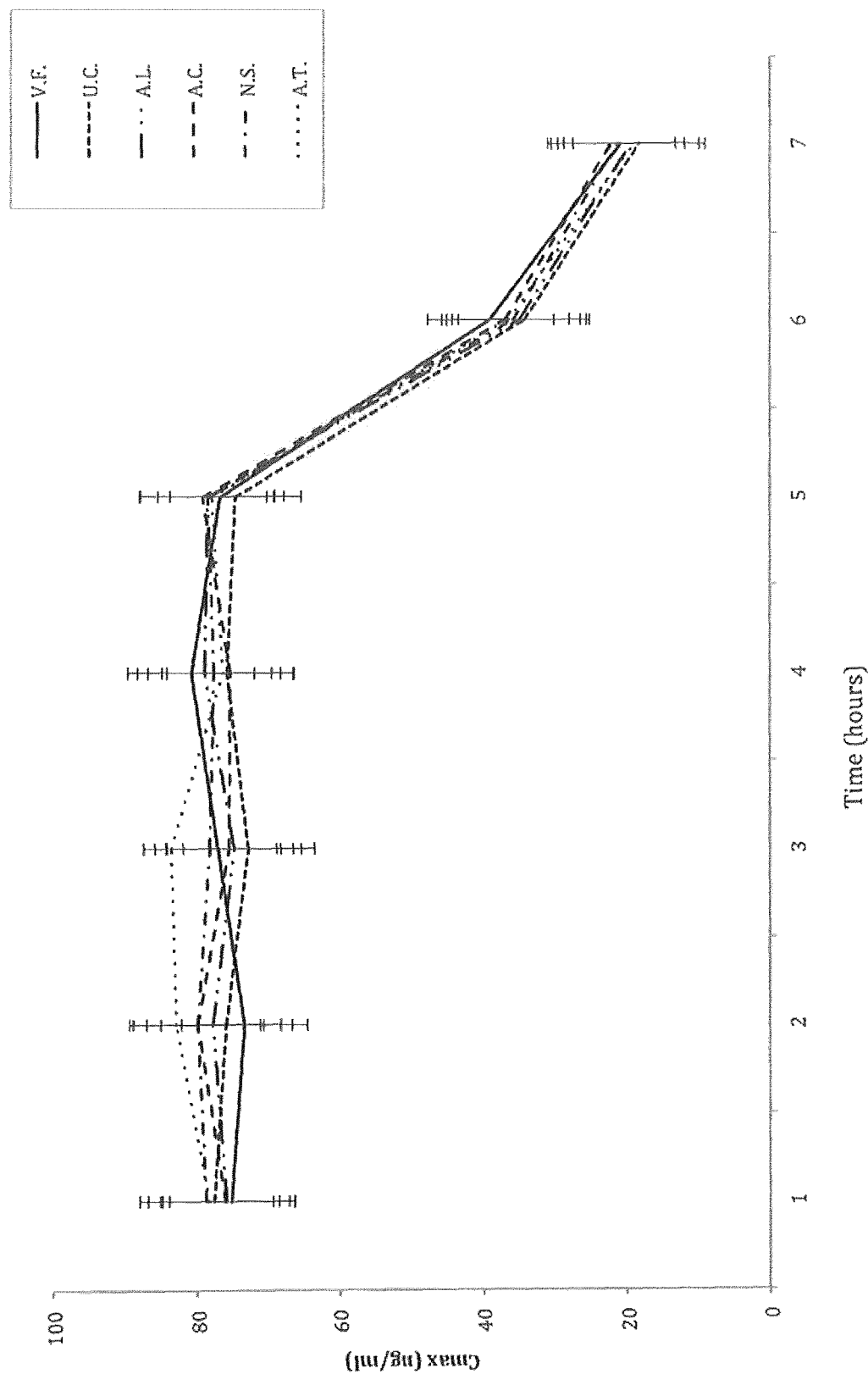

ANHYDROUS LIQUID MELATONIN COMPOSITION

The present invention relates to pharmacy and industrial bulk solution package of melatonin, an highly concentrated and versatile solution of melatonin in a substantially water-free carrier mixture of ethanol and polyethoxylated derivative, admixed in an optimal ratio to almost double melatonin solubility profile. The bulk solution is suitably designed to instantly prepare diluted compositions of injectable melatonin and different convenient melatonin preparations for other administration routes to humans, and also encompasses its specific preparation method. The invention is further characterized to yield the high concentration solution of melatonin up to and higher than 10.0% (w/v) and that the diluted solution thereof is suitable to deliver from 0.01 mg/ml up to 10 mg/ml of melatonin, preferably from 0.1 mg/ml to 5.0 mg/ml, and from 0.1 mg to 1000 mg melatonin/dose unit, preferably from 0.5 mg to 100 mg. The bulk solution of the invention does not contain preserving agents, is stable, and when intended for parenteral administration is made sterile, filled under GMP conditions, and conforms to pyrogens and bacterial endotoxins testing. A therapeutic affective dose of bulk solution of the invention can be admixed to a conventional infusion fluid and administered by constant IV infusion to humans to assure a concentration plateau of melatonin used as beneficial adjuvant therapy on life threatening diseases such as Ebola hemorrhagic fever (EHF) and Dengue hemorrhagic fever (DHF), but also as anti-oxidant/anti-aging and to ameliorate other health critical condition where a parenteral administration of melatonin is desirable. The invention encompasses also diluted solutions for oral and topic applications obtained from bulk solution as well.

BACKGROUND

Melatonin has fascinated the researchers due to its remarkable functional versatility and protective role in several pathophysiological conditions. Indeed, it plays a central role in wide physiological functions, like orchestrating circadian rhythms, along with the regulation of visual, cerebrovascular, reproductive, neuroendocrine, and neuroimmunological functions. Numerous studies have shown melatonin to promulgate a multitude of therapeutic functions that fight sepsis, neurodegenerative disorders, diabetes, biliary and pancreatic malfunctions, hepatotoxicity, cancer, inflammation, and oxidative stress. In addition, it is also a potent antioxidant and free radical scavenger. However, it is also known to regulate the levels of oxidative markers, endogenous antioxidant status, and proinflammatory cytokines. In humans, melatonin (N-acetyl-5-methoxytryptamine; CAS Number: 73-31-4; $C_{13}H_{18}N_2O_2$; molecular weight: 232.3) is an endogenous neurohormone secreted primarily from the pineal gland and to a lesser extent by extra pineal tissues such as the retina, harderian gland, and gastrointestinal tract. The non-clinical aspects of pharmacology (primary, secondary and safety pharmacodynamics of endogenous melatonin including in vitro and in vivo studies), pharmacokinetic and toxicokinetic studies of exogenous melatonin in animals are copiously available in the published literature and databank.

While current understanding of endogenous melatonin is substantial, the putative role and mechanisms of endogenous and exogenous melatonin remain unclear. To better understand the scope of the invention it is worth to introduce an overview on basic pharmacokinetic parameters of the drug substance melatonin and to outline its wide spectrum of potential applications and clinical indications, particularly by constant infusion. Melatonin can be administered in a variety of methods well known to those in the art, such as orally, intravenously and topically. Other uncommon uses of melatonin are described in recent publications such as local stimulation of osteointegration of dental implants and prostheses fixed with bone cement.

Melatonin Administered Orally.

When melatonin is administered orally to rats, dogs and monkeys at 10 mg/kg, the absolute bioavailability appeared to be moderate in rats and high in dogs and monkeys [Yeleswaram et al, 1997][1]. Oral administration to human volunteers of up to 3 times 80 mg of melatonin/person in one hour showed that the compound is rapidly absorbed and distributed throughout the human body, the half-life for the first part of the biphasic distribution phase being in the order of minutes. Highest melatonin values were measured in serum, 60 to 150 minutes after oral administration. Elimination of the molecule appeared to be slower than in rodents, since the concentration plateau lasted for several hours. The half-life of the first part of the biphasic elimination phase was found to be 20 to 50 minutes [Waldhauser et al, 1984][2]. When a lower dose of 3 mg of melatonin/volunteer was administered orally, an increase in serum melatonin within 20 minutes after oral administration was reported, followed by a rapid decrease at 240 minutes [Shirakawa et al, 1998][3]. Some authors [Fourtillan et al, 2000][4] reported a terminal half-life of 36 to 45 minutes when melatonin was measured in plasma after oral administration of a dose of 250 µg/person to human volunteers. In literature is reported that maximum blood and saliva concentrations of melatonin were reached 60 minutes after oral uptake of 100 mg of melatonin. The half-life of the molecule in blood was determined as around 41 minutes [Vakkuri et al, 1985][5]. When 2 or 4 mg melatonin/person were administered to human volunteers, only 15% of the ingested dose actually reached the systemic circulation. Most of administered melatonin disappears through the presystemic metabolization [DeMuro et al, 2000][6] and is excreted in urine as sulphatoxy-melatonin, the major conjugation product of 6-hydroxymelatonin. Unchanged melatonin renal clearance was lower than 1% [Fourtillan et al, 2000][4].

Melatonin Administered Intravenously.

Intravenous administration of melatonin to the rat has shown to result in a rapid distribution into plasma and all tissues of the animal, including cerebrospinal fluid and brain [Kopin et al, 1961; Vitte et al. 1988][7][8]. When the active substance was injected at 5 mg/kg, the apparent elimination half-life showed to be 19.8 minutes [Yeleswaram et al, 1997][1]. When melatonin was administered intravenously to the dog and the monkey at 3 mg/kg, the apparent elimination half-lives were measured to be 18.6 and 33.9 minutes respectively [Yeleswaram et al, 1997][1]. When a dose of 23 µg/person of melatonin was administered by intravenous injection to humans, an apparent half-life of 36 to 42 minutes in the systemic circulation was determined [Fourtillan et al, 2000][4].

The toxicokinetics of melatonin in man after intravenous administration are generally characterized by a very short distribution phase in the order of minutes, followed by a steady state concentration in the examined tissues (serum, blood, plasma, brain, etc.) in the order of a couple of hours, and a rapid elimination (half-life of about 40 minutes) after metabolization in the liver [Vitte et al, 1988; Mallo et al, 1990; Le Bars et al, 1991; DeMuro et al, 2000; Fourtillan et al, 2000][8][9][10][6][4]. The major metabolic pathway of melatonin in man has been identified as being the hydroxylation of position 6, followed by conjugation, primarily with sulfate (70%) and, to a smaller extent, with glucuronic acid (6%) [Kopin et al, 1961, Ma et al, 2005][7][12]. Melatonin 6-hydroxylation and O-demethylation have been identified as being mainly CYP1A2 mediated [Facciolá et al, 2001; Ma et al, 2005][11][12].

Melatonin Functions.

Melatonin has several putative functions including circadian rhythms of the body, therefore it is involved in the sleep-wake cycle, functions of the immune and cardiovascular systems, and cell regulation [Reiter et al, 2003; Vijayalaxmi et al, 2002][13][14], regulates the reproductive axis and is a natural antioxidant and potent free radical scavenger [Reiter et al, 2003; Korkmaz et al, 2009; Bonnefont-Rousselot et al, 2010][13][15][16]. Age-related reduction of melatonin has been correlated with disturbance of sleep, deterioration of health and chronic diseases related to oxidative damage, including cancer [Megdal et al, 2005; Reiter et al, 2003][17][13].

Historical review [Wettenberg, 1990][18] dealing with melatonin in humans show heterogeneous relationships between melatonin and other traits and increasing applications as medicament have been proposed to mitigate physiopathological conditions alike:

- sleep studies and biological rhythms;
- light, retinal sensitivity in humans and the circadian axis;
- surgical stress, anaesthesia;
- age-related studies (in the human foetus, in children, in elderly and as an antioxidant; the cyclic 3-hydroxymelatonin (3-OHM) biomarker; glucose regulation);
- depression and some other psychiatric disorders (fragmented rhythm in schizophrenia, obsessive-compulsive disorder [OCD], fibromyalgic syndrome, appetite-related peptides in ageing);
- sleep disturbance in depression, treatment of jet-lag, skin protection from ultraviolet radiation.

However, during the last decade researchers have continuously encouraged studies suggesting the use of melatonin in the management of serious life threatening conditions. Recent clinical studies (a selection since it would be impossible to list all of them) further suggest that many physiopathological conditions and disorders may benefit from the administration of melatonin, in view of its potent antioxidative effects, such as:

- glucose homeostasis [Karamitri et al, 2013][19];
- regulate the biliary functions [Glaser et al, 2014][20];
- exert important roles on the peripheral reproductive, cellular and organismal (maternal, placental and fetal) physiology [Reiter et al, 2014][21];
- ameliorate the physiopathology and influence the behavioural expression of autistic disorder [Tordjman et al, 2013][22];
- replace the decreased secretion to treat "sundowning" and other sleep wake disorders typical of Alzheimer Disease (Lin et al, 2013; Wade et al, 2014][23][24];
- regulate autophagy and mitophagy [Coto-Montes et al, 2012][25];
- correct Parkinson Disease sleep disorders [Suzuki et al, 2011; Downling et al, 2005; Srinivasan et al, 2011][26] [27][28];
- ameliorate sleep in older Intensive Care Unit (ICU) patients [Sterniczuk et al, 2014][29], improves sleep in Multiple Schlerosis (MS) [Adamczyk-Sowa et al, 2014][30], reduce sleep disturbances in Inflammatory Bowel Disease (IBD) patients [Kinnukan et al, 2013][31].

The increasing interest in melatonin is reflected in the histogram (FIG. 1) indicating the number of clinical trials per year that have been registered at "ClinicalTrials.gov" (a service of the U.S. National Institutes of Health) from 2004 to the date of offload in 2014. In fact, the growing interest in melatonin therapies in clinical trials being conducted for sepsis [Gitto et al, 2001][32], burns [Sahib et al, 2010][33], ischemic reperfusion [Dominguez-Rodriguez et al, 2007] [34], pre-surgical [Caumo et al, 2009; Borazan et al, 2010] [35][36], postsurgical [Gitto et al, 2004][37] and perioperative [Jarratt, 2011; Maitra et al, 2013] [38][39], cancer and cancer therapy adjuvant and immunology [Wang et al, 2012; Seely et al, 2011; Ghielmini et al, 1999; Bennukul et al, 2014; Martin et al, 2013; Carrillo-Vico et al, 2013][40][41] [42][43][44][45], preeclampsia [Aversa et al, 2012][46], cataract and glaucoma [Ismail et al, 2009][47], radiation protection [Berk et al, 2007][48], perinatal hypoxia and neonatal diseases [Ghitto et al, 2013; Alonso-Alconada et al, 2013][49][50] and in other unexplored therapies similarly requiring an high dosage regimen of melatonin, has not encountered satisfaction in view that a convenient pharmaceutical product of injectable quality melatonin is not yet commercially available. Often melatonin oral form is not an appropriate or usable administration route in critic health conditions. In fact, oral melatonin has high first pass metabolism (>85-90%) in the liver [Lane and Moss, 1985] [51], low and variable absolute human bioavailability (average 8.6% female, 16.8% male, range 1-37%) [Fourtillan et al, 2000][4] and high inter-subject dose variability (AUC curve of individual subjects varies by up to 25 times among subjects) [Waldhauser et al, 1984][2], so that constant infusion administration route of melatonin often will be the only viable choice for the deliver and control of an high dosage regimen.

Background of Injectable Preparations.

Patients hospitalized in critical care units with severe sepsis or septic shock, patients undergoing surgery, severe cases of burns and radiation exposure, patients undergoing oncologic therapies, newborn with perinatal or neonatal diseases, and in general patients in critical health conditions may not be able to ingest melatonin via oral route. A skilled person will reasonably recognise that the intravenous infusion of melatonin would represent the unique and most convenient route to treat those patents affected from life threatening diseases, wherein urgent, adequate (massive), accurate and constant dosages of melatonin are required. Hence, a skilled person shall further acknowledge that there is an objective and urgent need to provide the clinicians with pharmaceutical parenteral melatonin to treat those conditions and to extend its use to other unexplored fields of the medicine. Exemplary critical health conditions in humans which would substantially benefit from an infusion of high dosage regimen of injectable melatonin are:

Sepsis

Around 37,000 people die from sepsis in the UK each year, while severe sepsis strikes about 750,000 Americans, and as many as 8 million every year worldwide. It has been estimated that between 28 and 50 percent of these people die, far more than the number of U.S. deaths from prostate cancer, breast cancer and AIDS combined. The number of sepsis cases per year has been on the rise in the United States. Although the Surviving Sepsis Campaign (a performance improvement effort by hospitals across Europe, South America and the United States) has improved outcomes, the mortality rate still remains at 31% overall, and >70% in patients who develop sepsis-induced multiple organ failure. Anyone can get sepsis, but people with weakened immune systems, children, infants, so that frequent are paediatric intensive case patients with sepsis [Bagci et al, 2012][52] and the elderly are most vulnerable, so that sepsis is one of the most common case of death in intensive care units [Moroni et al, 2010; Alan et al, 2010; Srinivasan et al, 2012][53][54][55]. People with chronic illnesses, such as diabetes, AIDS, cancer and kidney or liver disease are also at increased risk, as are those who have experienced a severe burn or physical trauma. It has been recognised by leading clinicians that exogenous antioxidants may be useful in sepsis and more recently the potential for antioxidants acting specifically in mitochondria has been highlighted. In view of the above findings, a group of authors [Galley et al, 2014] [56] indicated melatonin as a potential therapy for sepsis and recently undertook a phase I dose escalation study in healthy volunteers to assess the tolerability and pharmacokinetics of 20, 30, 50, and 100 mg oral doses of melatonin capsules. For the phase I trial, oral melatonin was given to five subjects in each dose cohort (n=20). Melatonin was rapidly cleared at all doses with a median (range) elimination half life of 51.7 (29.5-63.2) minutes across all doses. However, there was a considerable variability in maximum melatonin levels within each dose cohort. In view of the high variability among the dose levels obtained following oral administration of capsules manufactured from chemically synthesized melatonin (dose mg/AUC ng/ml/min=20 mg: 1102-13616; 30 mg: 822-2491; 50 mg: 1812-8915; 100 mg: 4458-18229) a skilled person can reasonably conclude that an infusion of melatonin would result the more reliable method of administration for further studies on sepsis in order to assure in all patients the required therapeutic effective dose regimen, especially in paediatric patients or newborns.

Stroke

Each year, approximately 795,000 people suffer a stroke in the United States. About 600,000 of these are first attacks, and 185,000 are recurrent attacks. More than 140,000 people die each year from stroke and is the third leading cause of death. However, stroke is the leading cause of serious, long-term disability. Those figures can be worldwide extended with a certain approximation to other countries. A review paper [Shinozuka et al, 2013][57] supports the approach to deliver melatonin and to target melatonin receptors for neuroprotection in stroke. A number of studies have uniformly reported the important role of melatonin on neuroprotection in animal models of stroke. Experimentally induced stroke is exacerbated in pinealectomized rats [Manev et al, 1996; Kilic et al, 1999][58][59]. Melatonin administration after experimental stroke reduces infarction volume [Pei et al, 2003; Sinha et al, 2001][60][61]. Such a protective effect is seen in both gray and white matter [Lee et al, 2005][62]. Melatonin also reduces inflammatory response [Lee et al, 2007][63], cerebral oedema formation [Kondoh el al, 2009][64], and blood-brain barrier permeability [Chen et al, 2006][65]. Functionally, melatonin administration improves grip strength and motor coordination, and attenuates hyperactivity and anxiety [Kilic et al, 2008][66]. Melatonin secretion is known to decrease age dependently [Brzezinski, 1997][67], suggesting that if melatonin directly affects stroke, then aged people should suffer more strongly from insults of stroke. This may also be ameliorated with melatonin pretreatment. Studies in animal models of stroke have demonstrated that pretreatment of melatonin exerts anti-inflammatory effects and reduces infarction volume [Pei et al, 2002; Pei et al, 2002][68][69]. Numerous studies have documented melatonin-induced neuroprotection against ischemic and hemorrhagic stroke [Borlongan et al, 2000; Reiter et al, 2005][70][71]. In addition, authors describe a novel mechanism of action underlying the therapeutic benefits of stem cell therapy in stroke, implicating the role of melatonin receptors. Experiments warrant consideration to reveal an optimal melatonin treatment strategy that is safe and effective for human application. Neuroprotection shall be achieved in stroke with an higher dosage regimen of melatonin to be promptly and conveniently achieved intravenously by infusion.

Perioperative

Melatonin has some unique properties that are highly desirable in routine peri-operative care so that a new armamentarium of anaesthesiologist has been defined. Available clinical data show that preoperative melatonin is as effective as benzodiazepines in reducing preoperative anxiety with minimal action on psychomotor performance and sleep wake cycle. It may be considered as a safe and effective alternative of benzodiazepines as preoperative anxiolytic. It may have opioid sparing effect, may reduce intraocular pressure, and have role in prevention of postoperative delirium [Generali et al, 2013][72]. The short-term administration of melatonin is free from significant adverse effects also [Maitra et al, 2013][39]. However, the analgesic effects of melatonin have been also evidenced in clinics [Wilhelmsen et al, 2011; Azevedo de Zanette et al, 2014][73][74]. It would appear that patients on melatonin supplement should continue taking them perioperatively because there may be benefits [Jarratt, 2011][38]. It has been also observed that melatonin elicit anaesthesia so that it a suitable tool for patients critical care [Kurdi et al, 2013; Moroni et al, 2010; Alan et al, 2010][75][53][54].

Dialysis

Sleep disorders are common in kidney disease patients on dialysis due to a disturbance in their biological clocks and sleep complaints are common in a dialysis unit. In a survey dialysis patients reported sleep disorders (patients on chronic hemodialysis/HD and continuous peritoneal dialysis/PD) in about 52%. Patients reported trouble falling asleep [Holley et al, 1992][76]. In another survey about 83% patients reported sleep-wake complaints: disturbed sleep (51.8%) secondary to delayed sleep onset (46.5%), frequent night-time awakening (35.2%), restless legs syndrome and generalized (33.3% and 11.1% respectively), 72% admitted to early morning waking and daytime sleepiness (66.7%) [Walker et al, 1995][77]. Another publication confirmed similar sleep disorders in patients on HD and PD [Masaumi et al, 2013][78]. In an earlier publication some authors noted effects of nocturnal hemodialysis on melatonin rhythm (measured in saliva) and sleep-wake behaviour (Koch et al, 2009][79]. in a recent article seventy dialysis patients received melatonin or a placebo for one year. At three months, the previously shown beneficial effect of the short-term use of melatonin on sleep onset was confirmed. The investigators [Russcher et al, 2012][80] also noted improvement of sleep efficiency and sleep time. In contrast, at 12 months none of the measured sleep parameters differed significantly from placebo. However, the researchers observed that the benefits of melatonin on sleep persist over the long term, and that the long-term use of melatonin could improve patients' quality of life. Latter publications also stressed the need to evaluate whether exogenous administration of melatonin can improve the multiple sleep disorders in ESRD (end-stage renal disease) patients [Sharma, 2013][81] and that large randomized controlled trials are needed in order to establish its role in patient population on dialysis [Aperis et al, 2012][82]. In another randomized, double-blind cross-over clinical trial the effectiveness of melatonin versus placebo was tested in patient on conventional daytime HD. The 82 enrolled patients received exogenous melatonin dose set as one tablet at bedtime (3 mg tablet) [Edalat-Nejad et al, 2013][83]. The study suggested that melatonin emerge as a safe therapy for improving sleep quality (SQ) in HD patients. Therefore, in view of the high variance on absorption of oral doses, a skilled person could easily understand benefits and advantages deriving from a convenient parenteral administration melatonin solution admixed to the replacement fluid during dialysis.

Pancreatic Carcinogenesis

Pancreatic cancer has fatal prognosis because of the absence of early symptoms, late diagnosis and the resistance to radio- and chemotherapy. A recent review [Jaworek et al, 2014] [84] refers that in pancreatic carcinoma cell line (PANC-1) melatonin used at high doses affects the Bax/Bcl protein balance, and stimulates the expressions of caspase-9 and caspase-3, thus activating the mitochondrial pathway of apoptosis. Melatonin reduces angiogenesis and decreases proliferation of endothelial cells through inhibition of vascular endothelial factor (VEGF). In animal studies melatonin has been found to increase the efficacy of oncostatic drugs, to reduce the side effects of chemotherapy and to decrease morbidity. These observations suggest that melatonin at high doses could be potentially taken into consideration as the supportive treatment in the therapy of pancreatic cancer, although the effect of melatonin on apoptosis requires further study.

Snake Bite

The results demonstrated that melatonin efficiently alleviated *Echis carinatus* (EC) venom-induced haemorrhage and myonecrosis. It also mitigated the altered levels of inflammatory mediators and oxidative stress markers of blood components and in liver and kidney homogenates, documented renal and hepatoprotective action of melatonin. The histopathology of skin, muscle, liver and kidney tissues further substantiated the overall protection offered by melatonin against viper bite toxicities. The inability of antivenoms to block local effects and the fact that melatonin is already a widely used drug promulgating a multitude of therapeutic functionalities, its use in viper bite management is of high interest and should be seriously considered [Katkar el al, 2014][85].

Finally, despite the use of parenteral melatonin in other life-threatening diseases and conditions have not yet been described in literature, authors believe that also patients affected by other serious pathological conditions such as Ebola virus disease and Ebola hemorrhagic fever (EHF) and Dengue and severe Dengue could substantially be alleviated and benefit from the intravenous administration of an high dosage regimen of parenteral melatonin. Authors briefly describe hereby those pathological conditions and the preliminary results of open uncontrolled studies in volunteers.

Ebola (EVD) and Ebola Hemorrhagic Fever (EHF)

Ebola virus disease (EVD), formerly known as Ebola haemorrhagic fever (EHF), is a severe, often fatal illness in humans. EVD outbreaks have a case fatality rate of up to 90%, particularly in aged people. The virus is transmitted to people from wild animals and spreads in the human population through human-to-human transmission. Fruit bats of the Pteropodidae family are considered to be the natural host of the Ebola virus. The incubation period in humans, that is, the time interval from infection with the virus to onset of symptoms, is 2 to 21 days. All people infected show some extent of coagulopathy and impaired circulatory system symptomatology. Bleeding from mucous membranes and puncture sites is reported in 40-50% of cases, while maculopapular rashes are evident in approximately 50% of cases. Sources of bleed include hematemesis, hemoptysis, melena, and aforementioned bleeding from mucous membranes (gastrointestinal tract, nose, vagina and gingiva). However diffuse bleeding (i.e. heavy) is rare; occurrence is usually exclusive to the gastrointestinal tract. In general, development of hemorrhagic symptoms is indicative of a negative prognosis. However, contrary to popular belief, haemorrhage does not lead to hypovolemia and is not the cause of death (total blood loss is low except during labor). Instead, death occurs due to multiple organ dysfunction syndrome (MODS) due to fluid redistribution, hypotension, disseminated intravascular coagulation, and focal tissue necroses. Severely ill patients require intensive supportive care. No licensed specific treatment or vaccine is available for use in people or animals. Nowadays there is a real emergency in several West African countries where outbreaks are not under control of the local health authorities. There is no specific treatment or vaccine for Ebola fever. [WHO/Media centre: Ebola virus disease/Fact sheet n. 103/April 2014]. Authors observed that the hemorrhagic complications (hematemesis, hemoptysis, melena, bleeding from mucous membranes from gastrointestinal tract, nose, vagina and gingiva) could substantially benefit from a coadjuvant treatment with a therapeutically effective amount of intravenous melatonin, feasible with the bulk solution of the invention that make possible such high dosage regimen. The compassionate tests carried out on some patients admitted to an open study showed some favorable and promising outcomes in relation to the obtained benefit to general condition by the concentrated solution of the invention diluted in a saline fluid, preliminary results to be confirmed in a further monitored study.

Dengue and Severe Dengue (Dengue Hemorrhagic Fever/DHF)

The incidence of Dengue has grown dramatically around the world in recent decades. Over 2.5 billion people (over 40% of the world's population) are now at risk from Dengue. There are more than 100 millions new cases of Dengue fever every year throughout the world. Cases across the Americas, South-east Asia and Western Pacific have exceeded 1.2 million cases in 2008 and over 2.3 million in 2010 (based on official data submitted by Member States). Recently the number of reported cases has continued to increase. In 2013, 2.35 million cases of Dengue were reported in the Americas alone, of which 37,687 cases were severe Dengue. An estimated 500,000 people with severe Dengue require hospitalization each year, a large proportion of whom are children. About 2.5% of those affected die. The threat of a possible outbreak of Dengue fever now exists in Europe and local transmission of Dengue was reported for the first time in France and Croatia in 2010 and imported cases were detected in three other European countries. In 2012, an outbreak of Dengue on Madeira islands of Portugal resulted in over 2000 cases and imported cases were detected in 10 other countries in Europe. In 2013, cases have occurred in Florida (United States of America) and Yunnan province of China. Dengue fever is a severe, flu-like illness that affects infants, young children and adults, but seldom causes death. Dengue should be suspected when a high fever (40° C./104° F.) is accompanied by two of the following symptoms: severe headache, pain behind the eyes, muscle and joint pains, nausea, vomiting, swollen glands or rash, ecchymosis and petechiae. Symptoms usually last for 2-7 days, after an incubation period of 4-10 days after the bite from an infected mosquito. Severe Dengue is a potentially deadly complication due to plasma leaking, fluid accumulation, respiratory distress, severe bleeding, organ impairment. Warning signs occur 3-7 days after the first symptoms in conjunction with a decrease in temperature (below 38° C./100° F.) and include: severe abdominal pain, persistent vomiting, rapid breathing, bleeding gums, fatigue, restlessness, blood in vomit. The next 24-48 hours of the critical stage can be lethal; proper medical care is needed to avoid complications and risk of death. There is no specific treatment for Dengue fever [WHO/Media centre: Dengue and severe Dengue/Fact sheet n. 117/March 2014; MedlinePlus-NIH/National Institute of Health-USA/October 2012]. Authors observed that Dengue and severe Dengue, in addition to transfusion of fresh blood or platelets to correct the bleeding problems, could substantially benefit from a therapeutically effective infusion of intravenous melatonin at an high dosage regimen, feasible with the bulk solution of melatonin of the instant invention.

Background and Technical State of the Art

Despite the urgent need, medical opinion leaders, clinical doctors and personnel assigned to intensive care units can't afford parenteral preparations of injectable melatonin, since currently there is no commercially available intravenous (IV) dosage form of melatonin.

In fact, melatonin presents many crucial physicochemical aspects that shall be thoroughly considered when attempting to prepare an injectable composition of melatonin, as reported in the publications dealing with this technical challenge. In fact, there are significant technical challenges to overcome by formulating a composition of melatonin to be delivered intravenously. Despite several clinical studies and patents mention the possibility of using melatonin intravenously, the possibility of developing formulations at high concentrations of melatonin is still unsolved since no procedure used for the preparation of high dosages if melatonin, such as for instance at a 10% concentration, has been described in literature. Melatonin is slightly soluble in water (1.2-2.4 mg/ml) [Shida et al, 1994; Kandimalla et al, 1999] [86][87], is light sensitive [Andrisano et al, 2000][88], and unstable in aqueous solution [Daya et al, 2001][89]. Many studies have attempted to improve the melatonin solubility including the stability [Dayal et al, 2003; Lee et al, 1997; Lee et al, 1998][90][91][92] but without significant results. Therefore the possibility to prepare a stable solution with an high concentration of melatonin in water looks remote and almost impossible. However, there is evidence that melatonin solution gradually loses potency at all pH values and is not stable when exposed to light or oxygen. Some authors [Daya et al, 2001][89] studied the stability of melatonin solutions over a wide pH range (1.2-12) at room temperature and at 37° C. over a period of 21 days and found that from days 3 to 21 there was a gradual decrease in potency of melatonin throughout this range of pHs, with the decrease not exceeding 30%. The results of the study indicated that solutions of melatonin are relatively stable at room temperature (20° C.) and at 37° C. for at least 2 days. A sterile aqueous solutions of melatonin was prepared at various concentrations (1.0-113.0 micrograms/mil) in pyrogen-free glass vacuum vials and stored at room temperature, 4° C., and at −70° C. for up to 6 months [Cavallo et al, 1995][93]. It was found that the shelf life of melatonin was approximately 5 months at room temperature. The photodegradation products of melatonin were identified as 6-hydroxymelatonin (6-OHM) and N1-acetyl N2-formyl-5-methoxykynuramine (AFMK) and characterized them by NMR, FTIR and mass spectra identified [Andrisano et al, 2000][88]. Both of these compounds also occur endogenously in the body as products of normal hepatic metabolism and radical scavenging, and are not considered toxic. Consequently, many other technical factors shall be carefully considered when designing a stable solution of melatonin especially when an high concentration of melatonin is desired and when additionally the solution is intended for parenteral or intravenous administration to humans.

Two other different intravenous (IV) formulations for melatonin at a strength of 5 mg/ml (0.5%) have been reported in the prior art. The solubility of melatonin in propylene glycol (PG) solution increases slowly until 40% PG and then steeply increases. Solubility of melatonin increased linearly with concentration of 2-hydroxypropyl-beta-cyclodextrin (2-HPBCD/CAS 128446-35-5) without increase in PG. Melatonin solubility in mixtures of PG and 2-HPBCD also increased linearity but was less than the sum of its solubility in 2-HPBCD and PG individually. It was also found that the highest mixture of PG at 40% v/v and 2-HPBCD at 30% w/v had comparable solubility to the other vehicles at much higher concentrations, and had efficiency of melatonin solubilisation [Lee et al, 1997][91]. Melatonin in 10% PG was degraded 85 times more quickly than in aqueous solution without PG at −70° C. On the other hand, the degradation rate constant of melatonin in 2-HPBCD was not changed significantly when compared to water. None of the said solutions gives a satisfactory answer to to necessity to dispose concentrated solutions of melatonin for parental use, offering guarantees of adequate stability in aqueous solution.

EP0835652 (also published as U.S. Pat. No. 5,939,084) describes compositions containing melatonin for both pharmaceutical and cosmetic use, in aqueous solutions of PEG at different concentrations. However, the proposed approach is not without contraindications, since melatonin thus formulated was not stable either in quantitative terms, with loss of content, or in qualitative terms, with the development of degradation products. In addition, due to the presence of isoprene glycol, butylene glycol or propylene glycol in the composition the osmolality of the solutions presented don't have an acceptable level of osmolality for an injectable application or an oral and rectal administration. However, this patent indicates that the composition of one glycol and melatonin shall be a substantially ethanol-free aqueous phase, i.e. which shall not comprise ethanol or traces of ethanol insufficient to dissolve or improve the solubility of melatonin (claim 1).

EP1174134 describes a pharmaceutical or dietary composition for the treatment of cerebral infarction. Said pharmaceutical composition is administered via the oral route, in order to reduce the effects of the infarction. However, this type of administration presents a number of limits, since modest blood concentrations of melatonin are obtained due to its rapid hepatic metabolism. Consequently, low levels of the medicinal product are able to cross the blood-brain barrier and reach the damaged brain areas. Moreover, due to its poor solubility, a significant portion of the dose administered via the oral route is swallowed undissolved in saliva and is responsible for the low and variable bioavailability of melatonin via the gastrointestinal route. The evidence reported that patients with seizures of diverse origin show an alteration of the melatonin rhythm is supportive of its use also for this application.

In another small-scale clinical evaluation it has been found that intravenous (IV) administration of melatonin is appropriate in acute stroke [Cheung et al, 2006][94]. In the preliminary pharmacokinetic and safety study melatonin dissolved in propylene glycol was evaluated in adult male Sprague-Dawley rats, so that it was concluded that melatonin in propylene glycol elevates plasma levels of melatonin with no serious toxicity and that the preparation should be further evaluated in human patients.

Patent publication WO 2012/156565 describes a pharmaceutically acceptable injectable composition comprising water, propylene glycol (PPG) and melatonin, a derivative, a salt, a pro-drug or a solvate of same, which contains no other solvent, co-solvent or dispersing agent. The composition is used as injectable preparation as for instance for intravenous administration. The claimed composition is a mixture of water (from 50% to 95%) and propylene glycol (PPG) (from 5% to 50%). The percentage of PPG may vary from 10% and 30% of the total volume of the composition, while the suitable concentration is comprised between 20 and 30%, while the preferred one contain about 25% of propylene glycol. Melatonin concentration in the water/PPG mixture is variable from 5 to 50 mg/ml; suitable concentrations are between 7 and 20 mg/ml, and the preferred one contains about 10 mg of melatonin/ml of composition (composition expressed as %: melatonin 1.0%; PPG 25%, e.g. 250 mg PPG/mil). Example indicate that vials are sterilized by autoclaving (121° C. during 20 minutes). The stability of vials of the example (melatonin 1.0% solution) has been tested during 14 weeks, and the solution stored at 4° C. presents a small crystallization of the solution.

The recent patent publication WO 2013/068565 describes a powder for reconstitution before use as preparation for injection containing melatonin for the treatment of neonatal cerebral infarction. According to those authors, the invention is achieved by means of a powder for reconstitution dissolved in a mixture of water and polyalkylene glycol (PEG) in which the polyalkylene glycol is present in a quantity from 5 to 40% of the total volume, preferably in a quantity from 10% to 30%, such as to obtain a preparation for injection in the form of a solution containing melatonin. Melatonin composition of Examples from 2 to 13 describe that melatonin is mixed in different proportion with Tween 80® and/or Poloxamer 188® and/or lactose and/or leucine and/or glycine and/or mannitol. The spray-dryer operated at the inlet temperature of 150° C. allows to yield melatonin solid powder particles with certain mean diameter values (limits). The concentration achieved with 1 ml of the preparation of example 10 formulation are: 10.2 mg/ml melatonin (1.02%), 800 mg/ml PEG-400 (80.0%) and 200 mg water (20.0%). No mention is made by authors how powder particles are sterilized and how a endotoxin-free and pyrogen-free injectable preparation is obtained. Patent application further describes that in order to obtain a pharmaceutical form of melatonin that can be used in the treatment of cerebral infarction and in particular in neonatal cerebral infarction, the concentration of melatonin in the pharmaceutical form is from 2 mg/ml to 20 mg/ml (from 0.2 to 2.0%), preferably from 5 mg/ml to 15 mg/ml (from 0.5 to 1.5%) and more preferably from 8 mg/ml to 12 mg/ml (from 0.8 to 1.2%), being the solution also suitable for using in the treatment or prevention of perinatal asphyxia, neonatal cerebral infarction, treatment of sleep disorders in a paediatric patients, treatment of sleep disorders in Autism Spectrum Disorders (ASD) and for use in preanesthesia. Definitely, all prior art uses to dissolve melatonin essentially a binary system (water and PEG), and absent any rational criteria or strategy, other ingredients are also occasionally added, mainly surfactants (Tween 80®, Poloxamer 188®, lecithin or other alike), to yield emulsions, but without increasing the melatonin concentrations, thus remaining unsolved the other technical disadvantages. In fact, when storing the solutions of the prior art at a low temperature (e.g. 4° C.), with the aim to prolong their chemical stability, the ingredients may partially recrystallise with an opalescence or even with precipitations, adding the risk of a loss of active pharmaceutical substance assay and also of administering to the patient an intravenous solution containing suspended particles.

In view of the above results there is a technical evidence that the numerous attempts disclosed in the prior art to provide a stable and convenient pharmaceutical solution with high concentration of melatonin have failed, been either insufficient or inadequate to yield a conveniently stable composition containing an high concentration of melatonin suitable for parenteral administration.

Definitions

Unless defined otherwise, all technical and scientific terms used herein generally have the same meaning as commonly understood by one of ordinary skill in the art to which the instant invention belongs. More specific definitions are provided here below to better define the present invention.

As used herein "Bulk Solution" or "Pharmacy Bulk Package" is meant to be concentrated solutions as per monograph "Injections/definitions" of current USP and monograph "Parenteral preparations/Concentrates for injections or infusions" at page 787 of Vol. I of European Pharmacopoeia 8.0 and in the publications "Pharmaceutical Manufacturing Handbook Production and Processes" by Sayne Cox Gad, Wiley-Interscience, 2008 Published by John Wiley & Sons, inc. and "Pharmaceutical and Clinical Calculations", $2.^{nd}$ Edition, by Khan M. A. & Reddy I. K., Publisher CRC Press LLC, Chapter 5 "Calculation Involving Oral liquids/Calculations Associated with Bulk Preparations", pages 97-98/390, and "Remington: The Science and Practice of Pharmacy" Twentieth Edition, 2000, Chapter 11, page 117 Publisher Gennaro A R et al. A bulk solution or pharmacy or industrial bulk package is a container of a sterile preparation for parenteral use that contains many single doses. The contents are intended for use in a pharmacy admixture program and are restricted to the preparation of admixtures for infusion or, through a sterile transfer divide, for the filling of empty sterile syringes of other unitary or multi-dose containers. A bulk solution cannot be used directly as a medicinal product, but it shall be further diluted by a skilled artisan or a professional to yield the solution or the composition for actual use. Manufacturers and packagers of bulk packages prescription drugs do not have generally to use special packaging since the bulk solution can be also further diluted and repackaged by the pharmacists or health professionals, licensed pharmaceutical industry or by qualified personnel in clinics or hospitals. Sometimes it will be beneficial to make a bulk solution of certain medications that may be prepared in bulk to be dispensed later or to be used as stock solutions to prepare further medicinal products. A bulk solution is usually a solution at a higher concentration, sometimes at the highest as possible, that can be diluted later to make other diluted solutions intended to present special technical advantages (handling, stability, economicity and others, that could be used to yield further diluted solutions. Hence the definitions concentrated solution or pharmacy bulk package or industrial bulk package can be indifferently used.

As used herein, therefore, the term "Diluted Solution" is meant to include those intermediate or final solutions that can be promptly and handily obtained from said bulk solution (as previously defined) conveniently diluted with one or more inert fluids to yield a lower concentration, as also suggested in the exemplary cases of the above cited publications. Diluted solutions can be also achieved to handily admixing a bulk solution to a diluent that does not contain any active ingredient or to another solution containing another active substance.

As used herein the term "Parenteral preparations", thus including parenteral solutions, as also defined in The International Pharmacopoeia, 4.th Edition 3.rd 2006, Supplement, 2013, World Health Organization, is meant to be sterile, pyrogen-free liquids (solutions, emulsions, or suspensions) or dosage forms containing one or more active ingredients, packaged in either single-dose or multi-dose containers. There are four main forms of parenteral preparations: injections, intravenous infusions (large volume parenterals), powders for injections, and implants. Certain injections and intravenous infusions may be presented in the form of sterile concentrated solutions, which must be suitably diluted before use. Parenteral preparations comply with paragraph 3.2 Test for sterility. All intravenous infusions and those injections where the volume to be injected in a single dose is 15 ml or more must comply with paragraph 3.4 Test for bacterial endotoxins or, where justified, with paragraph 3.5 Test for pyrogens.

As used herein "Melatonin" (identification acronym: MLT) is meant to be the active substance conforming to the specifications and analytical methods of the monograph "Melatonin" at page 1534 of The United States Pharmacopeia USP 36/NF 31 Volume 1, Official as from May 1, 2013, with the prescribed content not less than 98.5% and not more than 101.5% of $C_{13}H_{16}N_2O_2$ calculated on the dry basis, and also conforming to the monograph "Melatonin" published in British Pharmacopoeia 2012, with a content not less than 98.0% and not more than 102.0% of $C_{13}H_{16}N_2O_2$ calculated on the dry basis. More particularly, as used herein, the term "Melatonin Extra-Pure" (identification acronym: MLTEP) is meant to include the pharmaceutical active substance fully conforming to the specifications and analytical methods of the above mentioned monographs "Melatonin" but with a much more stringent purity content not less than 99.0% and not more than 101.0% of $C_{13}H_{16}N_2O_2$ calculated on the dry basis.

As used herein "Ethanol anhydrous" (also improperly referred as Ethanol absolute or dehydrated that at 20° C. is not less than 99.5% volume/volume or 199 proof) is meant to be the product identified in the monograph 04/2014:1318 of European Pharmacopoeia (EP) Supplement 04/2014, that have undergone pharmacopoeial harmonization (see chapter 5.8 Pharmacopoeial harmonization of current EP). Therefore Ethanol anhydrous quality, as intended in the current invention, meets or exceeds the current EP/BP/USP/JP specifications, and additionally is sterile.

As used herein "Ethanol (96 percent)" is ethanol ($C_2H_6O$; MW 46.07) 95.1 percent v/v to 96.6 percent v/v calculated from the relative density at 20° C. is not less than 95.0% volume/volume or 192 proof) is meant to be the product identified in the monograph 04/2008:1317 of European Pharmacopoeia (EP) Supplement 01/2014, that have undergone pharmacopoeial harmonization (see chapter 5.8 Pharmacopoeial harmonization of current EP). Therefore Ethanol (96 percent; 192 proof) quality, as intended in this invention, meets or exceeds the current EP/BP/USP/JP grade specifications, and additionally is naturally sterile and GMP grade.

As used herein the term "Macrogolglycerol hydroxystearate" is meant to be a polyethoxylated derivative complying with the specifications of the monograph 01/2008:1083 of European Pharmacopoeia 8.0 Ed. page 2664, with the special proviso that the nominal value (moles of ethylene oxide ethoxilating trihydroxystearyl glycerol) is comprised from 15 to 60, more preferably between 40-45; the same product is published as "Hydrogenated Polyoxyl Castor Oil" in the monograph in British Pharmacopoeia 2009, Volume I, page 377.

As used herein the term "Polyoxyl 40 Hydrogenated Castor Oil" is meant to be the type of polyethoxylated derivative (equivalent to the above mentioned "Macrogolglycerol hydroxystearate"), whereas the nominal value is restricted to 40-45, as prescribed in the Official Monograph of The United States Pharmacopoeia Ed. 36/The National Formulary Ed. 31 (USP36/NF31), Volume 1, page 2156, Official from May 1, 2013.

As used herein "Macrogolglycerol ricinoleate" refers to a polyethoxylated derivative, inert ingredient complying within the specifications of monograph 01/2008:1082 European Pharmacopoeia 8.0 Ed. page 2665; this ingredient is also published as monograph "Polyoxyl Castor Oil" in British Pharm. 2009, Volume I, page 376.

As used herein "Polyoxyl 35 castor oil" is meant to be the polyethoxylate derivative equivalent to "Macrogolglycerol ricinoleate" whereas with the nominal value is 35, thus complying with the specifications of Monograph of The United States Pharmacopoeia Ed. 36/The National Formulary Ed. 31 (USP36/NF31), Volume 1, page 2156, Official from May 1, 2013.

As used herein the term "Macrogol 15 hydroxystearate" is meant to be the mixture described and complying with the specifications of the monograph 01/2008:2052 European Pharmacopoeia 8.0 Ed. page 2655; it contains a mixture of mainly monoesters and diesters of 12-hydroxystearic (12-hydroxyoctadecanoic) acid and polyethoxylated 12-hydroxystearic acid (nominal value is 15 moles of ethylene oxide).

As used herein the term "Polyoxyl 15 Hydroxystearate" is meant to be the derivative (equivalent to "Macrogol 15 hydroxystearate") complying with the specifications of the Official Monograph of The United States Pharmacopoeia Ed. 36/The National Formulary Ed. 31 (USP36/NF31), Volume 1, page 2156, Official from May 1, 2013.

As used herein, any of the above polyethoxylated derivatives (hereinafter defined also with the acronym "PED") can be used indifferently in the present invention, whereas, if no differently specified, the term PED also meant a mixture of two or more of the above inert ingredients thereof.

As used herein the term "Water for injections" (Aqua pro Injectione) is meant to be the vehicle for aqueous injections (The International Pharmacopoeia, 4.th Edition 3.rd 2006, Supplement, 2013, World Health Organization; European Pharm. 8.0 Ed. Monograph 1/2009:0169). It should be freshly distilled by the process described under "Aqua pro Injectione", be free from carbon dioxide, and comply with paragraph 3.4 Test for bacterial endotoxins.

As used herein, the general term "Pharmaceutical grade water" is meant both the "Water highly purified" and the "Water purified" (the second including "Purified water in bulk" and "Purified water in containers") as per monographs 01/2009:1927 and 01/2009:0008 of European Pharmacopoeia 8.0 Ed., 01/2014 or equivalent.

As used herein the term "Sodium Chloride Intravenous Infusion" or "Sodium Chloride Injection" or less commonly defined as "Physiological saline" is meant to identify a sterile solution of sodium chloride water for injection, both ingredients complying with the applicable pharmacopoeia or better with monographs harmonized monographs as published in EP, JP and USP. It contains no antimicrobial agents. A 0.9% solution in water is iso-osmotic, and thus in most cases isotonic with serum.

As used herein the general term "Hypertonic saline solution", for which there is not available an official definition, is a low volume hypertonic solution of sodium chloride normally available in two strengths, the former of which is more commonly administered: 3.0% NaCl having 513 mEq/Liter and 5.0% NaCl having 856 mEq/Liter, while NaCl solutions less commonly used are 7.0% (1220 mEq/Liter) and 23.4% (approx 4000 mEq/Liter) both of which are used (via a central catheter also known as a "central line"), often in conjunction with supplementary diuretics in the treatment of traumatic brain injury. Hypertonic saline may also contain additional ingredients, such as in the case of hypertonic saline with hydroxyethyl starch (7.2% NaCl with 6.0% hydroxyethyl starch 200,000/0.5), as they are increasingly used in emergency therapies.

BRIEF DESCRIPTION

FIG. 1 shows, by histogram, the increasing interest in melatonin, as measured by the number of clinical trials per year registered at "ClinicalTrials.gov." FIG. 2 graphically illustrates the concentration of infused melatonin plotted against time. The present invention provides a substantially water-free composition of pharmacy and industrial bulk package of melatonin at a concentration up to and higher than 10.0% (weight/volume) with satisfactory chemical and physical stability even at low temperatures. Said versatile solution is then conveniently and handily diluted at the time of use with pharmaceutically acceptable fluids to yield intravenous infusion for administration to humans, but also for oral and local applications. The substantially water-free composition of pharmacy and industrial bulk package surprisingly provides a parenteral preparation of melatonin at a concentration up to and higher than 10.0% intended to be delivered intravenously in humans, whereas at the present no such high dosage form of melatonin is commercially available, thus filling the instant invention the existing gap between prior technology (unable to provide a suitable technical solution) and the objective clinical requirements evidenced in the world-wide publications. More preferably the new technique of the invention discloses that said bulk solution of injectable melatonin is surprisingly achieved when melatonin is dissolved in a substantially water-free carrier mixture of ethanol and polyethoxylated derivative admixed in optimal ratio so that melatonin expresses its highest solubility profile, almost the double of that with the prior art. In another embodiment the instant invention further discloses the multi-steps sequence to admix ingredients to yield the highly concentrated bulk solution of melatonin of the invention obtained by firstly kneading melatonin and the polyethoxylated derivative to yield a pasty mass which thereafter is dissolved into a convenient amount of substantially water-free ethanol to yield the desired solution at the unique concentration of 10.0%.

It is a further embodiment of the invention that the pasty mass contains melatonin and the selected polyethoxylated derivative in a precise ratio to yield the optimal concentration range of melatonin in the bulk solution higher than 10.0% (e.g. 100 mg/ml), and even above, being said ratio purposely intended to maximize the solubility and stability patterns of the active in the fluid carrier, thus achieving optimal physicochemical characteristics of stability which is required for pharmaceutical products.

It is therefore a further technological object of the invention to provide a pasty mass and a bulk solution thereof, whereas the active substance is Melatonin (MLT), preferably the defined Melatonin Extra-Pure (MLTEP) when a parenteral solution is desired. It is a further preferred embodiment of the invention that the polyethoxylated derivative is selected among Macrogolglycerol hydroxystearate (also Polyoxyl 40 Hydrogenated castor oil) with nominal value 40-45, Macrogolglycerol ricinoleate (also Polyoxyl 35 castor oil) and Macrogol 15 hydroxystearate (also Polyoxyl 15 hydroxystearate) of pharmaceutically approved quality as defined. It is yet a further regulatory benefit that the pharmaceutical monographs of the selected polyethoxylated derivatives are published in the most common pharmacopoeias (see Definitions). in fact, their use already allowed for pharmaceutical and medicinal practice by the regulatory authorities of many countries represents a further technical advantage, this avoiding to perform long and expensive toxicological studies. This additional guarantee of quality assurance and regulatory compliance is further appreciable in view that melatonin bulk solution of the invention is mainly intended for infusion purposes, while additional medicinal applications are also feasible, as disclosed hereinafter. In another technical embodiment, the invention encompasses the multi-steps sequence to admix the ingredients; melatonin is firstly thoroughly kneaded with an equivalent mass of the selected polyethoxylated derivative to yield the pasty mixture. It is a further a characterizing embodiment that the ratio of the ingredients of the pasty mass has been experimentally determined by authors to express the higher solubility rate in ethanol. Authors has also determined that the optimal ratio melatonin/polyethoxylated derivative is comprised between ranges of 0.90-1.10 (w): 0.90-1.10 (w), more preferably 1:1 (w/w).

In an additional preferred object the invention, in a second step of the process the pasty mass is carefully diluted into an appropriate volume of substantially water-free ethanol to yield the concentrated melatonin bulk solution of the invention. Another technical preference of the invention is to provide a substantially water-free bulk solution of melatonin, in order to minimize the interaction of melatonin with water and the other ingredients and to avoid the reported instability of melatonin with the combined presence of water and oxygen, so that the composition of the invention is conveniently stable during the storage period comprised between its production and subsequent use. Stability is also achieved by avoiding the use of preserving agents, since ethanol itself is an efficient preservative agent. A skilled person knows that preservatives are reputed to cause intolerance and other allergic disorders or symptoms, so that their use in parenteral preparations is generally undesired and even banned. However, ethanol keeps the bulk solution of melatonin at a biological pH and does not influence or modify the pH of other fluids used to dilute the bulk solution.

It is further preferred that the bulk solution of the invention is simply sterilized by passing it on conventional membrane filters (sterilizing filtration) thus avoiding other physical methods detrimental to melatonin stability, such as thermal (heat) and radiation methods (gamma rays and UV light). A further feature of the invention encompasses that the preparation of the bulk solution is performed in compliance with current GMP conditions and more particularly that the medicinal product containing the parenteral bulk solution is sterile and in compliance with the required microbiological quality (pass the bacterial endotoxin and pyrogens limit test). In fact, it is an additional feature of the invention to provide a pharmacy and industrial bulk solution package of concentrated melatonin solution (up to and higher than 10.0%) to be then advantageously used to instantly and handily prepare convenient diluted pharmaceutical compositions of lower concentration of melatonin to be either intended for parenteral administration, preferably infusion, to humans and for oral and topical applications as well. According to one embodiment the pharmacy and industrial bulk solution package of concentrated melatonin and of the diluted preparations thereof are further filled into appropriate unitary or multiple dose dispensing containers characterized to deliver the defined liquid form dose of melatonin solution up to or higher than 10.0%, as sought for the intended pharmacologically or clinically expected use.

It is an another embodiment that the bulk solution package of melatonin solution up to or higher than 10.0% (w/v) and of the diluted solution as well, comprise very different containers and delivery systems already available on the market for the intended clinical purpose.

The bulk solution package is further characterized to contain either a concentrated solution of melatonin equal to or higher than 10.0% (w/v) than can precisely deliver 10 mg of melatonin per 0.1 ml and multiples thereof or a diluted solution thereof that can suitably and accurately deliver from 0.01 mg/ml up to 10 mg/ml of melatonin, preferably from 0.1 mg/ml to 5.0 mg/ml, and from 0.1 mg to 1000 mg melatonin/dose unit, preferably from 0.5 mg to 100 mg.

The concentrated bulk solution and the diluted solutions of lesser strength of the invention are suitably filled in a primary container closed with convenient cooperating components (either stopper or delivery system, fitted by pressure, screwed or crimped on and the like) compatible with ethanol, while the primary components are made from non-transparent material rigorously light-resistant, preferably amber glass ampoules, vials or bottles, to conveniently provide absolute protection from UV light and gas-resistant to retain nitrogen, the purge process gas preferably saturating the container (before closing) to protect melatonin from the air, being melatonin easily oxidable as well.

In another embodiment, the bulk solution of concentrated melatonin equal to or higher than 10.0% (w/v), at the time of use is more conveniently and handily diluted to yield solutions of known concentration of lesser strength for actual use, thus avoiding frequent dilution errors, improving the accuracy and precision of the dilution operation, saving preparation time, so that the diluted solution at the sought concentration and/or intended dosage is more appropriate and safe for its immediate clinical use, more advantageously when IV infusion route of administration is required.

In a further technical achievement of the instant invention, the mass (mg) of melatonin expressed per volume (ml) of bulk solution higher than 10.0% (e.g. 100 mg/ml) produces that proportionally a lower volume of melatonin solution of the invention is required to deliver the same mass (mg) of melatonin. The lower volume represents a further advantage over the solutions described in the prior art using different technology and methods. The high concentration of melatonin in the bulk solution allows to reduce significantly the volume of ethanol, so that the volume of ethanol administered to patients will result negligible in relation to the high dose of delivered melatonin and meaningless in consideration of the life threatening pathologies sometimes requiring therapeutically effective amounts of melatonin (some pathologies are from 100 to 300 mg daily or even above). In other words, when 1 ml bulk solution containing 100 mg melatonin is dissolved in 1000 ml of fluid, constituting the same volume of diluted solution of melatonin, the concentration of ethanol will result less than 0.1% (v/v). The diluted liquid solutions of the invention containing lesser strengths of melatonin, when resulting from the admixture with conventional replacement fluids, can be safely administered to humans by infusion, or, when admixed in a suitable fluid carrier with auxiliary ingredients, can be further processed, packed and stored to yield additional pharmaceutical and nutraceutical compositions for oral use by other administration routes for their intended use, whenever a therapeutic effective dose of melatonin is required. In fact, in another embodiment the bulk solution of melatonin 10.0% is further conveniently diluted into a volume of Sodium Chloride Intravenous Infusion to yield a clear a sterile solution at the desired concentration of melatonin which can be promptly and handily administered intravenously to humans at an infusion speed appropriate to the age also in relation to the clinical intended effect.

The invention also encompasses the specific use of stock solution at 10.0% of melatonin to yield a diluted solution by handily pouring 1.0 ml (100 mg melatonin) in 1 liter of Sodium Chloride Intravenous Infusion to deliver by constant IV infusion to humans a total dose of 100 mg during a certain period to yield the high desired concentration plateau of melatonin.

The invention further encompasses a diluted solution of melatonin that can conveniently an handily obtained suitably diluting said bulk solution with one or more inert fluids to yield lower concentrations of melatonin, being the diluted solution intended both for medicinal products (intended as a continuation therapy of a parenteral treatment) and nutraceutical compositions suitable for oral use, whenever a therapeutic effective dose of melatonin is required by oral administration, including prophylactic purposes as it may be directed. A diluted solution of melatonin can be also applied topically to body surfaces such as skin or mucous membranes of the oral cavity, whenever a therapeutic effective dose of melatonin is required locally. The diluted solution of the invention can be achieved handily admixing an amount of bulk solution either to a suitable liquid diluent that does not contain any active ingredients or to a solution containing one or more active substances chemically compatible with melatonin. Similarly, other active ingredients chemically compatible with melatonin (compatibility tables are freely available on line) can be also simultaneously administered by infusion. The diluted compositions for enteral and topical uses shall be packed in a convenient dispensing container primarily to preserve melatonin from light and from oxidation (photodegradation and oxidation are the most common source of degradation in current commercial products) in order to ensure a stability period from the production date up to a 24 months or even more storage period, and also to provide the most suitable dispensing system in relation to the intended dosage and site of application. Special sprayers or nebulizers such as those equipped with airless dosing pumps equipped with push-nozzle or throat dispenser or based on bag on valve technology, equipped with a suitable dispenser, are those preferred as delivery systems for the diluted solution of the invention.

An additional object is to provide pharmaceutical compositions as above and further described useful for the above purposes. These and other objects will be readily apparent to the ordinary artisan from consideration of the invention as a whole.

Surprisingly, in another embodiment the authors have determined that when the bulk solution containing melatonin at 10.0% can be promptly and suitably diluted into a convenient volume of Sodium Chloride Intravenous Infusion (generally 1 ml of bulk solution of 100 mg/ml in a 1000 ml infusion fluid that yields a clear, sterile isotonic diluted solution of the invention) can be advantageously administered intravenously to humans whenever a therapeutic effective dose of melatonin is required in life threatening conditions such as those caused from Ebola hemorrhagic fever (EHF) and Dengue hemorrhagic fever (DHF), where authors believe that high plasmatic levels of melatonin could favourably correct bleeding problems, promote platelets and red blood cells production in the body, enhance a general protective effect on the nano and capillary system, reduce ecchymosis, petechiae and generalized rush, significantly inhibit the production and reduce the accumulation of proinflammatory cytokines with a remarkable benefit for the tissues, organs and for the entire body presenting such critical health conditions.

However, the possibility to deliver by constant IV infusion to humans and therefore to make bio-available overnight a cumulative dose of 100 mg and an highly concentrated plateau of melatonin, makes the bulk solution the preferred delivery system for strong anti-oxidant and anti-ageing prevention designs and treatments.

DETAILED DESCRIPTION AND PREFERRED EMBODIMENTS

Therefore the present invention provides a substantially water-free bulk solution, also defined pharmacy or industrial bulk package, as a liquid preparation of melatonin, containing at least:

a) melatonin (MLT) quantitatively at the concentration up to or higher than 10.0% weight/volume of the bulk solution;

b) a polyethoxylated derivative selected among macrogolglycerol hydroxystearate, preferably polyoxyl 40 hydrogenated castor oil, or macrogolglycerol ricinoleate, preferably polyoxyl 35 castor oil, or macrogol 15 hydroxystearate, also polyoxyl 15 hydroxystearate, or a mixture thereof (hereinafter defined as PED), whereas the preferred mass ratio MLT/PED is comprised between the variable ranges 0.90-1.10 (weight):0.90-1.10 (weight) and the preferred optimal ratio is 1:1 (weight/weight);

c) ethanol al least 10 volumes;

intended for parenteral administration after convenient dilution, preferably intravenous, to humans, but also for oral and local applications.

The bulk solution of the invention is further characterized that it does not contain other solvent, cosolvent, dispersing agent or surfactant.

It is almost preferred when a substantially water-free bulk solution or pharmacy/industrial bulk package of melatonin, contains at least:

a) melatonin (MLT) whereas preferably is Melatonin Extra-Pure (MLTEP) at the concentration of 10.0% weight/volume of the bulk solution;

b) the polyethoxylated derivative (PED) is preferably macrogolglycerol hydroxystearate (polyoxyl 40 hydrogenated castor oil), with restriction of the nominal value 40-45, or macrogol 15 hydroxystearate (polyoxyl 15 hydroxystearate), with nominal value 15; and c) ethanol whereas preferably is Ethanol anhydrous harmonized quality and additionally sterile;

wherein also the auxiliary ingredients are pharmaceutically acceptable.

It is almost unique that the bulk solution of the invention delivers at least up to and even more than melatonin 100 mg/ml of bulk solution. Such an high concentration of melatonin has never been described in the prior art, even for an aqueous solution and such high concentrated liquid dosage form of melatonin is not commercially available.

In a further characterizing feature the mass of the selected PED is at least comprised between 90.0% and 110.0% of the mass of MLT, being the most preferable combination when PED mass is equal to MLT, having authors determined that the optimal ratio of 1:1 (w/w) maximizes the solubility and the stability patterns of the active ingredient in the carrier, while the surprising physicochemical stability patterns are achieved as well.

Authors have demonstrated that the pasty mass of MLT/PED at ratio 1:1 (w/w) is expressing the highest solubility rate of melatonin up to and higher than 10.0% (w/v), when said semisolid mixture is dissolved with ethanol in the volume sufficient up to 100.0%. However, it is a further preferred characterizing embodiment of the bulk solution the ratio of MLT/PED/Ethanol of 1:1:10 (w/w/v), with individual and relative variations comprised from about 90.0% to about 110.0% for each ingredient, as it may be suitably applicable.

In fact, authors have experimentally determined that the high concentration of melatonin up to and higher than 10.0% of the bulk solution of the invention can be surprisingly achieved only when MLT is firstly combined with PED in a precise ratio and thoroughly kneaded to yield a pasty mass, that in a second step is dissolved in ethanol by observing the above characterizing ratio as well. It is worth to underline that said semisolid mixture of MLT/PED (at the ratio 1:1) is not soluble in water, while MLT/PED semisolid mixture is easily dissolved in at least 10 volumes of ethanol.

Contrarily, either by admixing 1 mass of MLT and ethanol (10 volumes) and by adding to the obtained suspension 1 mass of PED, or also vice versa when dissolving 1 mass of PED in ethanol (10 volumes) and then adding 1 mass of MLT to the solution, it is not possible to achieve the clear, transparent and stable (at 5° C. storage without precipitate) solution characterizing the invention, which is then obtainable by the using sequence of the invention (firstly semisolid mixture MLT/PED and then dissolution of the semisolid paste in at least 10 volumes of ethanol). The experimental findings characterizing the bulk solution of the invention are summarized in Table n. 1A, Table n. 1B and Table n. 2.

TABLE n. 1A

Comparative solubility tests (20° C.)
Variable element: ratio MLT/PED/ETHANOL

Test Invention Variable ratio: MLT + PED = MLT/PED + Ethanol (ET) = see Notes Ratio: Variable

| MLT (w/g) | PED (w/g) | Ethanol (v/ml) | RATIO MLT/PED/ET | Notes |
| --- | --- | --- | --- | --- |
| 0.5 | 0.5 | 10.0 | 1:1:20 | Clear, limpid & stable at 5° C. |
| 0.5 | 1.0 | 10.0 | 1:2:20 | Solution but changes colour |
| 0.5 | 1.5 | 10.0 | 1:3:20 | Solution but changes colour |
| 1.0 | 0.5 | 10.0 | 2:1:20 | Opalescent & precipitate |
| 1.0 | 1.0 | 10.0 | 1:1:10 | Clear, limpid & stable at 5° C. |
| 1.0 | 1.5 | 10.0 | 2:3:20 | Turbid & Changes colour |
| 1.5 | 0.5 | 10.0 | 3:1:20 | Very turbid & precipitate |
| 1.5 | 1.0 | 10.0 | 3:2:20 | Turbid & precipitate |
| 1.5 | 1.5 | 10.0 | 3:3:20 | Turbid & very instable |

TABLE n. 1B

Comparative solubility tests (20° C.)
Variable element: Sequence of production steps Test Invention Sequence 1: MLT + PED = MLT/PED + Ethanol = Bulk solution
Ratio: (1:1:10) (w/w/v)

| MLT (w/g) | PED (w/g) | MLT/PED Consistency | Ethanol (v/ml) | Notes |
|---|---|---|---|---|
| 0.5 | 0.5 | Pasty mass | 10.0 | Clear, limpid & stable at 5° C. |
| 0.8 | 0.8 | Pasty mass | 10.0 | Clear, limpid & stable at 5° C. |
| 0.9 | 0.9 | Pasty mass | 10.0 | Clear, limpid & stable at 5° C. |
| 1.0 | 1.0 | Pasty mass | 10.0 | Clear, limpid & stable at 5° C. |
| 1.1 | 1.1 | Pasty mass | 10.0 | Clear, limpid & stable at 5° C. |
| 1.2 | 1.2 | Pasty mass | 10.0 | Clear, limpid & stable at 5° C. |
| 1.3 | 1.3 | Pasty mass | 10.0 | Clear, limpid & instable at 5° C. |
| 1.4 | 1.4 | Pasty mass | 10.0 | Turbid & slight precipitate |

Comparative Sequence 2: MLT + Ethanol = MLT/Ethanol + PED = see Notes
Ratio: (1:10:1) (w/v/w)

| MLT (w/g) | Ethanol (v/ml) | MLT/Ethanol Consistency | PED (w/g) | Notes |
|---|---|---|---|---|
| 0.5 | 10.0 | solution | 0.5 | Suspension |
| 1.0 | 10.0 | turbid | 1.0 | Suspension |

Comparative Sequence 3: PED + Ethanol = PED/Ethanol + MLT = see Notes
Ratio: (1:10:1) (w/v/w)

| PED (w/g) | Ethanol (v/ml) | PED/Ethanol Consistency | MLT (w/g) | Notes |
|---|---|---|---|---|
| 0.5 | 10.0 | solution | 0.5 | Turbid, milky |
| 1.0 | 10.0 | solution | 1.0 | Opalescent suspension |

TABLE n. 2

Comparative solubility tests (20° C.)
Variable element: Solvent

Comparative Test Water: MLT + PED = MLT/PED + Water = Suspension
Ratio: (1:1:20 and 1; 1; 10) (w/w/v)

| MLT (w/g) | PED (w/g) | MLT/PED Consistency | Water (v/ml) | Notes |
|---|---|---|---|---|
| 0.5 | 0.5 | Pasty mass | 10.0 | Suspension |
| 1.0 | 1.0 | Pasty mass | 10.0 | Suspension |

Comparative Test Water/Ethanol: MLT + PED = MLT/PED + W/E = Suspension
Ratio: (1:1:10:10 and 1:1:5:5) (w/w/v/v)

| MLT (w/g) | PED (w/g) | MLT/PED Consistency | W/E (v/ml) | Notes |
|---|---|---|---|---|
| 0.5 | 0.5 | Pasty mass | 10.0 | Suspension |
| 1.0 | 1.0 | Pasty mass | 10.0 | Suspension |

Blank Tests (20° C.)

Blank Test 1: MLT + PED = see Notes
Ratio: (1:1) (w/w)

| MLT (w/g) | PED (w/g) | MLT/PED Consistency | Ethanol (v/ml) | Notes |
|---|---|---|---|---|
| 0.5 | 0.5 | Pasty mass | — | Pasty mass |
| 1.0 | 1.0 | Pasty mass | — | Pasty mass |

Blank Test 2: MLT + Ethanol = see Notes
Ratio: (1:20 and 1:10) (w/v)

| MLT (w/g) | Ethanol (v/ml) | MLT/Ethanol Consistency | PED (w/g) | Notes |
|---|---|---|---|---|
| 0.5 | 10.0 | Solution | — | Solution, opalescent at 5° C. |
| 1.0 | 10.0 | Suspension | — | Suspension & precipitate |

Blank Test 3: PED + Ethanol = see Notes
Ratio: (1:20 and 1:10) (w/v)

| PED (w/g) | Ethanol (v/ml) | PED/Ethanol Consistency | MLT (w/g) | Notes |
|---|---|---|---|---|
| 0.5 | 10.0 | solution | — | solution |
| 1.0 | 10.0 | solution | — | solution |

Basic features resulting from Table 1/A and characterizing the bulk solution of the invention is that the mass of the selected PED is at least comprised between 90.0% and 110.0% of MLT mass and vice versa, having authors further determined that optimal ratio is 1:1 (w/w) and that additionally, when MLT/PED are admixed in the ratio 1:1 (w/w), the invention is further characterized that the resulting pasty mass (MLT/PED) is able to express the highest solubility rate of melatonin in the bulk solution when the semisolid admixture is later dissolved with ethanol. However, authors have found that a more preferred embodiment characterizing the bulk solution of the invention in when a ratio MLT/PED/Ethanol of 1:1:10 (w/w/v) is used, with individual and relative tolerance of the quantity of each ingredient comprised from about 90.0% to about 110.0%, as it may be applicable. Table 1/B further confirms that the sequence the production steps sequence is also preferred embodiment characterizing the bulk solution. Results from Table 2 are further characterizing the bulk solution of the invention since the pasty semisolid mass of MLT/PED (1:1) is not soluble in water, both either at the ratios 1:50 (w/v), 1:20 (w/v) and also at 1:10 (w/v), e.g. at 2.0%, 5.0% and 10.0% (w/v) respectively. However, the solvent mixture water (W)/ethanol does not solve the above solubility problem: the mixture MLT/PED/W/Ethanol is at the ratio 1:1:10:10 (w/w/v/v) yields a opalescent and instable suspension that precipitates lowering the temperature; also when MLT/PED/W/Ethanol is in the ratio 1:1:5:5 (w/w/v/v) a thick milky suspension is obtained.

Therefore, it is further characterising the invention that the substantially water-free bulk solution contains ethanol (96 percent/192° Proof). It is further preferred the use of ethanol dehydrated, as hereinabove defined, to yield 100% volume of bulk solution, and it is most preferable when harmonized USP/BP/EP/JP ethanol anhydrous (also defined absolute, dehydrated) that meets or exceeds the harmonized specifications is used. However the characterizing absence of water in the bulk solution avoids the known instability of melatonin in presence of moisture. Furthermore, another advantage is that ethanol prevents that lower temperatures, as those of storage and distribution for pharmaceutical products having areas at controlled refrigerated temperature usually at 5° C. (±3° C.), could result critic and affect also the bulk solution causing unexpected precipitation. It is a further advantage characterizing the bulk solution or pharmacy/industrial bulk package containing the liquid preparation of concentrated melatonin that ethanol, differently from water, does not contain any ions (OH⁻ or H⁺) so that pH is very close to neutrality so that the bulk solution has a negligible influence on the aqueous solution to which is admixed.

Due that the solution of the invention is mainly intended for parenteral use, as for instance the intravenous administration of significant amounts of melatonin to humans, authors have also determined that MLT quality shall be conform to USP/BP monographs (see Definitions) and that the MLT characterizing the bulk solution of the invention shall have the most stringent specification so that assay and purity content shall not be less than 99.0% and not more than 101.0% of $C_{13}H_{16}N_2O_2$ calculated on the dry basis, quality conventionally identified with acronym MLTEP (Melatonin Extra-Pure). Therefore, another characterizing aspect of the bulk solution of the invention is that MLTEP shall comply with the required microbiological quality (it passes the bacterial endotoxin and pyrogens test limits), since after crystallization (this production step of MLTEP is not claimed as part of the invention), the crystalline MLTEP is further washed with a bactericidal alcohol to remove bacterial endotoxins and pyrogens, so that the dried powder, after passing the conventional limit tests for bacterial endotoxin and pyrogens, has been classified by authors as conform to bacterial endotoxin and pyrogen test limits. Authors have further determined that MLTEP characterizing the bulk solution of the invention, whenever intended for parenteral use, mainly intravenous, shall comply with the endotoxins requirement of max 300 I.U./gram.

In another aspect bulk solution of the invention is further characterized that the selected PED is preferred among macrogolglycerol hydroxystearate, preferably polyoxyl 40 hydrogenated castor oil, with nominal value 40-45, or macrogolglycerol ricinoleate, preferably polyoxyl 35 castor oil, or macrogol 15 hydroxystearate, also polyoxyl 15 hydroxystearate, with nominal value 15, or a mixture thereof (hereinafter defined as PED), whereas the preferred mass ratio MLT/PED is comprised between the variable ranges 0.90-1.10 (w):0.90-1.10 (w) and the preferred optimal ratio is 1:1 (w/w). For additional specification authors make direct reference to Definitions and to the official pharmacopoeias.

The bulk solution of the invention is further characterized to combine MLT with the selected PED and ethanol, with the advantages reported by the authors. The selected PED consistently enhance the solubility of MLT in ethanol up to and higher than 10.0% (w/v), while ethanol has a stabilizing effect on the selected PED of the bulk solution. In fact, the congealing/freezing point of the selected PED is in the range of 20-30° C., so that an aqueous solution containing a concentration of about 10% of the selected PED has the risk to precipitate when stored at a controlled storage temperature of 5° C. (±3° C.), as sometimes it may be required for stock and distribution areas for pharmaceutical products. This risk has not shown using the concentrated solution of melatonin since ethalo has a suitable anti-freezing activity. It is yet a further desirable feature that each selected PED has its own specific monograph published in the leading pharmacopoeias (as per Definitions). Hence, the regulatory and technical advantage characterizing its presence is that the biological and pharmaceutical suitability of each selected PED has been already recognised and licensed in the pharmaceutical and medicinal practice by the regulatory authorities of many countries. However, this represents a further quality guarantee and assurance of the regulatory compliance of each selected PED, so that the bulk solution and the diluted solutions of the instant invention mainly intended for parenteral administration to humans do not presents limits to its use, also when bulk and diluted solutions are directed to other medicinal or nutritional applications as disclosed hereafter. However, authors have determined that also the selected PED, as MLT, shall comply with microbiological enumeration test (TAMC max $10^{-2}$ CFU/g; TYMC max 10 CFU/g) and with the endotoxins requirement max 300 I.U./gram.

A further characterizing embodiment of the production method of the bulk solution of the invention is the sequence to admix the constituents in the process to yield the desired bulk solution or pharmacy and industrial bulk package liquid form of concentrated melatonin. Despite authors have already found that the most preferred actuation of the invention is achieved when the composition contains the optimal ratio 1:1:10 (w/w/v), between MLT, PED and ethanol, respectively (with individual and relative mass variations comprised from about 90.0% to about 110.0% for each ingredient as it may be suitably applicable) they further experimentally determined that a precise sequence of steps to admix the components to yield the desired bulk solution is required. In fact, the first step for production of the bulk solution is characterized that the equally weighed masses of PED and MLT are placed in a suitable vacuum mixer/homogenizer, where nitrogen is used as purge process gas, and are thoroughly admixed at about 21° C. until a pasty mass is obtained (operation takes about one hour). In the second step the semisolid paste is then removed quickly from the mixing bowl and placed into a suitable vacuum-operating stirred tank (nitrogen is used as purge process gas) where the prescribed amount of ethanol is added to the pasty mass and the mixture is gently admixed until complete dissolution to yield the bulk solution of the invention. Once the assay of melatonin in the bulk solution stored the tank has been determined, a skilled operator shall determine the quantity of absolute ethanol to be added to the mass of the solution (the tank is equipped with a weighing system) to yield the exact concentration of melatonin. The technical area of the production operations shall be equipped with a lightening system with UV filters, to avoid the inconvenience of photodegradation of melatonin.

As evidenced from the results summarized in Table 2, by changing the sequence of the production steps, it is not possible to achieve the feature of the bulk solution of the invention. That is to yield a concentrated bulk solution of melatonin at 10.0% (w/v) If fact, the inverted sequence to admix the ingredients does not increase the solubility profile of melatonin (melatonin concentration remain much lower than the target of the invention) so that a milky suspension or a thick opalescent solution or a pasty precipitate are obtained. However, due to relevant presence of ethanol in the composition, the production shall be performed in a specific antideflagrant area, and antideflagrant equipment and services shall be operated as well. The invention further encompasses preparation steps performed according to current and applicable GMP conditions to yield a sterile bulk solution complying also with the endotoxins requirement max 300 I.U./gram. According to one embodiment the pharmacy/industrial bulk solution package of concentrated melatonin is either further filled into appropriate unitary or multiple dose dispensing containers characterized to deliver the defined liquid form dose of melatonin solution equal or higher than 10.0%, as sought for the pharmacologically or clinically intended use, or further conveniently diluted to yield suitable diluted solution at the desired concentration of melatonin to be then used instantly or also suitably packed for short, medium or long term storage, as it may be necessary.

It is a another embodiment that the bulk solution package of melatonin solution equal or higher than 10.0% (w/v) comprises also different containers, closured and delivery systems already commercially available for the intended use purpose.

The pharmacy and industrial bulk solution package is further characterized to be suitably packed to contain a concentrated solution of melatonin at 10.0% (w/v) that either delivers 10 mg melatonin per 0.1 ml, or that the diluted solution thereof precisely and suitably delivers from 0.01 mg/ml up to 10 mg/ml of melatonin, preferably from 0.1 mg/ml to 5.0 mg/ml, and from 0.1 mg to 1000 mg melatonin/dose unit, preferably from 0.5 mg to 100 mg, so that a wide spectrum of clinical applications can be covered.

The high concentration of melatonin in the bulk solution allows to reduce significantly the volume of residual ethanol in the diluted solution, so that the administered volume of ethanol to patients will then result negligible in relation to the high dose of melatonin and meaningless in consideration of the life threatening pathologies sometimes requiring therapeutically effective amounts of melatonin (some pathologies require from 100 to 200 mg daily or even more) to meet the desired high dosage regimen.

The concentrated bulk solution of the invention is presented in the desired volume into a primary unit-dose or multi-dose container, as for instance vials, sealed with a suitably cooperating component compatible with ethanol (stopper crimped with an a crimped on aluminium capsule, or fitted by pressure or screwed and the like), while the primary container is made from non-transparent material, Lopez (IGL-1) to protect nonsteatotic and steatotic liver grafts against cold ischemia-reperfusion injury, as suggested in recent scientific publications and the like), its is mainly intended to yield instantly the diluted solutions of the invention thereof either for immediate parenteral use, preferably intravenously to humans, or to be then packed in suitable containers for oral and local applications. Hence, the water-free bulk solution or pharmacy/industrial bulk package containing the liquid preparation of concentrated melatonin shall pass tests for assay, clarity, pH, sterility, bacterial endotoxin, and stability, as already anticipated and as illustrated in details in the exemplary studies. The production of the bulk solution shall be performed under stringently controlled clean room class 10,000 for mixing and the solution, and class 100 for the filling operations after sterilization. The formulation, specifications, physicochemical characteristics and evaluation of stability patterns of the bulk solution will be disclosed in illustrative examples. Due to its unique and versatile composition, the bulk solution presents several advantages that can be summarized, but to mention some of them without limitation, as follow: higher concentration of MLT equal or higher than 10.0% (w/v) (achieved with a surprising combination of ingredients at a certain ratio), bactericide (without adding preserving agents) and almost at the neutral pH of ethanol, and stable during long storage even at controlled temperature without risk of crystallization, minimal quantity of PED per ml of bulk solution (e.g. 100 mg PED/ml), with a relatively very low dose of ethanol compared to MLT (100 mg MLT/1.0 ml ethanol). Differently, other aqueous (not ethanolic) solutions described in the prior art are containing melatonin only at 1-3% and PEG up to 40% of the total volume of the liquid used (e.g. up to 400 mg PEG/mil). Some comparative figures are shown in the following Table n. 3.

TABLE n. 3

| Basic ingredients | | Instant invention | | WO 2012/156565 | | WO2013/068565 Reconstituted solution | |
|---|---|---|---|---|---|---|---|
| | | Solution | | Solution | | from powder | |
| Ingredient | volume or mass | range | pref. | range | Pref. | range | Example |
| Melatonin | w/mg | 100 | 100 | 0.5-50 | 10 | — | 10 |
| PED | w/mg | 100 | 10 | — | — | — | — |
| Ethanol | v/ml | 1000 | 1000 | — | — | — | — |
| Water | mg | — | — | 50-900 | 750 | — | 200 |
| PPG | mg | — | — | 50-500 | 250 | — | — |
| PEG | | — | — | — | — | 50-400 | 800 |
| Others Ingredients | | — | — | — | — | Several & variable number & quantity | |
| Total | | 1000 ml | 1000 ml | 1000 mg | 1000 mg | — | — | preferably a small vial from pharmaceutical grade dark-amber glass type 1, rigorously light-resistant to conveniently provide photoprotection and also able to retain nitrogen, the purge process gas, intended to saturate the container during the filling process with the aim to prevent melatonin oxidation. Despite the bulk solution of the invention can be used rarely directly as it is (as for instance to film dental implants and prostheses fixed with bone cement, and mixed to bone cement of dental pre implants as well, to locally stimulate the osteointegration, as already published, or to deposit multilayer films on hearth stents to prevent aggregation after implant, or to be added in a suitable quantity to the preservation solutions UW (University of Wisconsin) to prevent kidney grafts cold preservation injury and institute Georges Surprisingly, the technological features of the bulk solution of the invention become more impressive at the time that the highly concentrated solution of melatonin is conveniently and handily diluted to yield solutions of known concentration and lesser strengths for actual parenteral use, mainly intravenously, to humans, thus avoiding frequent dilution errors, improving the accuracy and precision of the dilution operation, saving preparation time, so that the diluted solution at the sought concentration and/or intended dosage is more appropriate and safe for its immediate clinical use or for ameliorate the preservation of grafts organs. The bulk solution can yield the diluted solution of lower concentration of melatonin of the invention by simply adding one diluent or inert fluids, as designed, being said diluted solution of the invention also intended for medicinal products (as a continuation therapy of a previous parenteral treatment), or nutritional compositions suitable for enteral use, whenever a therapeutic effective dose of melatonin is required by oral administration, including prophylactic purposes as it may be directed. Diluent may be an inert fluid that does not contain any active ingredients or a solution containing inside one or more active substances chemically compatible with melatonin.

The diluted solution is almost one/tenth of the bulk solution and authors were surprised that the enhanced solubility of melatonin of the bulk solution is maintained also in the diluted solution, and the stability as well, even at a lower concentrations of ethanol, so that authors have formulated the hypothesis, which has to be confirmed by further studies, that the diluted solution represents a so called "glass solution" system, where the active substance is molecularly dispersed in amorphous state so that the stability system is perfectly maintained insofar as the drug substance is much below the saturation solubility.

The lesser strengths pharmaceutical liquid solution of the invention may be safely administered parenterally, preferably intravenously, to humans, or can be further processed, packed and stored to yield additional pharmaceutical and nutritional compositions for enteral use by other suitable administration routes for their intended use, whenever a therapeutic effective dose of melatonin is required. In fact, the bulk solution of melatonin 10.0% may be further conveniently diluted by a skilled artisan, an health professional, clinician or pharmacist, into a convenient volume, preferably from 500 ml up to 1 liter, of Sodium Chloride Intravenous Infusion to yield a clear diluted solution (sterile, isotonic/isomolar, without influencing or modifying its original physiological pH) with the desired concentration of melatonin which can be promptly and handily administered intravenously to humans at an infusion speed appropriate to the age and to the content of sodium. Therefore, the diluted solution, readily prepared directly from a portion of the stock solution of the invention, is available to patients whenever an intravenous administration of melatonin is required by the clinicians in the pathological conditions of the referred publications, such as for instance, Intensive Care Unit (ICU), Sepsis, Stroke, Perioprative, Dialysis, Pancreas, Oncology, Snake bite and the like, but also for other unexplored medicinal uses.

It is another embodiment of the invention that when 1.0 ml bulk solution containing MLT at 10.0% (e.g. 100 mg MLT) is diluted into the convenient volume of 500 ml of Sodium Chloride Intravenous Infusion the diluted solution can be advantageously administered intravenously to humans whenever a therapeutic effective dose regimen of 100 mg/day of MLT is required and achieved with a continuous infusion of melatonin at 20 mg/h which allows to assure an unique plateau blood coverage of MLT during several hours, as experimentally determined in a preliminary study.

Subjects 6 healthy male Caucasian volunteers aged 20 to 30 with normal sleep-wake cycle were recruited for the study after written consensus and trial was conducted according to Declaration of Helsinki. A complete history and physical examination were performed on all subjects prior to initiation of the study. Participants were not enrolled if they were receiving any medications during the study period. Participants were excluded if they had a history of melatonin use during the previous year, significant systemic medical disease, body weight greater than 30% of ideal, or used tobacco products. Subjects were also screened with blood chemistry panel and urinalysis prior to study initiation. Volunteers' parameters are listed here below.

| Subjects | Age/years | Weight/Kg | Height/cm |
|---|---|---|---|
| 1 V.F. | 23 | 73 | 178 |
| 2 U.C. | 25 | 69 | 168 |
| 3 A.L. | 21 | 77 | 185 |
| 4 A.C. | 22 | 75 | 180 |
| 5 N.S. | 23 | 73 | 177 |
| 6 A.T. | 24 | 74 | 183 |
| Mean | 23 | 73.5 | 178.5 |

Materials

Tested product (100 mg melatonin/ml solution extracted from 5 ml vial) was prepared according to Example 4. The drawn solution (1 ml) was diluted into 500 ml of Sodium Chloride Intravenous Infusion bottle.

Study Design

The trial on volunteers consisted of one intervention day. Four working days before the intervention day, the subjects were instructed to adapt to a standardized sleep cycle, no caffeine and no alcohol intake in the two prior days. At the intervention day, the volunteers had intravenous catheter inserted in cubital veins bilaterally (one for infusion and the other for blood withdrawal). Volunteers were monitored with hourly measurement of blood pressure, temperature and heart rate. Blood samples at time 0 have been withdrawn for baseline control. Melatonin infusion rate (20 mg/hour) was started at 1.00 p.m. until 6 p.m. (5 hours).

Blood Samples and Analysis

Blood samples were drawn hourly for analysis up to 8 p.m. and sent to analysis. The used analytical method for the measurement of melatonin in serum derived from the renown publication (Waldhauser et al, 1984)[2]. Results are tabulated in Table 4.

TABLE 4

Melatonin Cmax concentrations in individual subjects

| ID N° | Subject | Cmax (ng/ml) after 1 h | Cmax (ng/ml) after 2 h | Cmax (ng/ml) after 3 h |
|---|---|---|---|---|
| 1 | V.F. | 74.9433333 ± 0.31134118 | 73.1733333 ± 0.922894 | 76.9066667 ± 0.33501244 |
| 2 | U.C. | 77.5066667 ± 0.45081408 | 75.7833333 ± 0.38070111 | 72.61133333 ± 0.48809152 |
| 3 | A.L. | 75.7533333 ± 0.47056703 | 77.6133333 ± 0.26350206 | 74.6966667 ± 0.8315247 |
| 4 | A.C. | 75.8033333 ± 0.66123622 | 79.7566667 ± 0.25006666 | 75.3033333 ± 0.38591882 |
| 5 | N.S. | 78.5766667 ± 0.33650161 | 79.7566667 ± 0.81291656 | 77.9266667 ± 0.75500552 |
| 6 | A.T. | 78.2766667 ± 0.63319297 | 82.7266667 ± 0.47815618 | 83.5666667 ± 0.5500303 |

TABLE 4-continued

Melatonin Cmax concentrations in individual subjects

| ID N° | Cmax (ng/ml) after 4 h | Cmax (ng/ml) after 5 h | Cmax (ng/ml) after 6 h | Cmax (ng/ml) after 7 h |
|---|---|---|---|---|
| 1 | 80.6166667 ± 0.32254199 | 76.5466667 ± 0.37527767 | 38.9266667 ± 0.39272552 | 20.7233333 ± 0.17214335 |
| 2 | 75.6366667 ± 0.5688878 | 74.4766667 ± 0.4424176 | 34.18666672 ± 0.5986932 | 18.2233333 ± 0.47162838 |
| 3 | 78.83333333 ± 0.74648063 | 78.3433333 ± 0.63129497 | 34.9066667 ± 0.89745938 | 19.3466667 ± 0.64500646 |
| 4 | 75.1966667 ± 0.68412962 | 78.9566667 ± 0.74567643 | 36.7766667 ± 0.26025628 | 22.0766667 ± 0.46177195 |
| 5 | 77.4766667 ± 0.45632591 | 78.3366667 ± 0.48232078 | 35.6033333 ± 0.44601943 | 21.11333333 ± 0.85991 |
| 6 | 76.2466667 ± 0.97592691 | 77.8333333 ± 0.44117268 | 36.5566667 ± 0.50816664 | 19.0666667 ± 0.40673497 |

CONCLUSIONS

The continuous infusion of melatonin at 20 mg/h allows to assure a steady state blood concentration during 5 hours in the range from 70 ng/ml to 85 ng/ml, as evidenced in FIG. 2.

Surprisingly, in another embodiment the authors have determined that when the bulk solution containing melatonin at 10.0% is diluted into a convenient volume of Sodium Chloride Intravenous Infusion (in general 1.0 ml of bulk solution containing 100 mg melatonin is diluted in 500 ml or better in 1 liter), the diluted solution can be advantageously administered intravenously to humans whenever a therapeutic effective dose of melatonin is required as adjuvant in life threatening conditions such as those caused from Ebola hemorrhagic fever (EHF) and Dengue hemorrhagic fever (DHF), where authors believe that high plasmatic levels of melatonin could favourably correct bleeding problems, promote platelets and red blood cells production, enhance a general protective effect on the nano and capillary system, reduce ecchymosis, petechiae and generalized rush, significantly inhibit the production and reduce the accumulation of proinflammatory cytokines with a remarkable benefit for the tissues, organs and for the entire body presenting such critical health conditions. A diluted solution of melatonin can be also applied topically to body surfaces such as skin or mucous membranes of the oral cavity, whenever a therapeutic effective dose of melatonin is required locally.

The diluted solution of melatonin of the invention, is the most desirable alternative to the solid forms of melatonin (soft gelatin capsule and tablet) for non collaborating patients for hospitalization/condition (ICU, assisted ventilation, multiple sclerosis), for age groups (paediatric and old patients), non-psychiatric inability (difficulty to swallow or tracheal and oesophageal obstruction), autistic disorders, patients with reduced capacity or cognitive disorders (Alzheimer's, Parkinson's diseases, psychiatric conditions), but to mention some of them, factors affecting patient treatment adherence.

When the diluted solution of melatonin of the invention is delivered by oral route, directly into the mouth, (as liquid or drop or preferably in the nebulised form) with the aim to accurately deliver a precise dose of melatonin, swallowed naturally with the saliva, the unit dose of melatonin in the solution shall be studied carefully in relation to melatonin concentration, delivered volume and patient age group.

However, authors have also experienced that the better accuracy of dosage of the device and that the most convenient delivery into the mouth can be achieved by using a metered pump system, that delivers the required volume, and a suitable cooperating actuator, preferably a mouth dispenser, both currently available on the market. Therefore, while in an adult the current dosage range of melatonin (at night-time) generally varies from 3 mg (or multiples thereof) up to 10 mg (at night-time), when using a pump dosing 0.1 ml of solution, in order to deliver a range of 1-3 mg of melatonin per pump actuation, the concentration of melatonin in the diluted solution of the invention shall be in the range from 10 to 30 mg/ml.

By considering that the recommended dosage in adolescents suffering from autism spectrum disorders (ASDs) and attention-deficit hyperactivity disorder (ADHD) varies from 1 to 3 mg of melatonin (or multiples) at night-time [Malow B, 2012; Humphreys J, 2014][95][96], a diluted solution at a concentration of melatonin 10 mg/ml, when dispensed with a 0.1 ml metered pump, conveniently delivers 1 mg melatonin per each actuation. If in both cases another pump dispensing a different volume is used and/or a different dose of melatonin per actuation is desired, the concentration of melatonin can be proportionally adjusted in the diluted solution of the invention as it will be readily apparent to an ordinary artisan.

Despite PED has a very little odour and in aqueous solutions is almost tasteless and melatonin as well, in view that the diluted solution of the invention is intended for oral administration in adolescents and aged patients, authors considered that attention shall be also paid to the taste compliance, but basically to the physico-chemicals characters, and therefore the final diluted solution shall finally present the following specifications and characters:

(a) melatonin shall remain homogeneously dissolved in the diluted solution, so that bulk solution active substance and ingredients shall not react with the auxiliary ingredients;

(b) the diluted solution shall biologically acceptable to the oral and upper oesophageal mucosa (pH from 6.5 to 7.5);

The diluted solution of the invention shall remain stable, clear and transparent without precipitates and contaminants, so that it would be advisable to avoid chemical incompatibilities, such as using parabens with a pH greater than 8.0, using ethylendiaminetetraacetic acid and some of the salts thereof which attack the calcium of the dentine ("Handbook of Pharmaceutical Recipients", 4th edition, 2003, American Pharmaceutical Association, page 226, paragraph 14, Safety) or using colorants to avoid loss of colour during ageing and so on. After several attempts, authors have found that the diluted solution of the invention can be conveniently achieved by using:

(c) pharmaceutical grade water as basic diluent, but with the adoption of special precautions such as special unit package and storage conditions of the finished product to avoid photodegradation and hydrolysis;

(d) moderate quantities of auxiliary ingredients such as glycerol (E422), xylitol (E967), neohesperidine DC (E959), but also sorbitol (E420), mannitol (E421), advantame (E969) saccharin and its salts (E054), acesulfame potassium (E950), salt of aspartame-acesulfame (E062), as non-cariogenic sweeteners.

Optionally natural essences or flavours may be also added to the solution.

Nevertheless, with regard to the quality and quantity thereof stated in the Examples, these auxiliary ingredients are the result of careful optimisation which was not carried out casually but also involves an inventive step, regardless they are not claimed.

The invention also encompasses the production process of the diluted solution, as defined above, and the apportioning thereof into the final packaging ready for distribution, sale and use by the patient, said process comprising the following sequence of operations:

(1) transfer in a dissolution tank with stirrer and weighing system (jacketed at about 15° C. and using nitrogen as a purge gas) of the accurately measured volume (or weight) of bulk solution;
(2) adding half volume (or weight) of pharmaceutical grade water and stir to homogenization (about 15 minutes);
(3) add rapidly the exact quantity of auxiliary ingredients already dissolved in about one tenth (1/10) of the pharmaceutical grade water/ethanol mixture and stir to homogenization (about 10 minutes);
(4) add the remaining quantity of pharmaceutical grade water up to the defined volume (or weight) and stir to homogenization (about 15 minutes);
(5) withdrawn a sample for analytical purposes (assay of melatonin), close and purge with nitrogen the dissolution tank until the diluted solution is released from the quality control laboratory.

The solution according to the invention is prepared in the above-stated sequence using the methods and machinery conventionally used in the pharmaceutical sector, but this is neither mandatory nor does it limit the invention itself. Indeed, adjustments remain possible with regard to the specific formulation used, the overall volume of the batch to be prepared, while nevertheless obtaining a result which is comparable overall with that of the invention itself. The diluted solution of the invention is apportioned into a suitable packing system for preservation, distribution, sale and further use by patients. The preferred container for the diluted solution of melatonin is a multidose container (preferably a bottle from amber glass or plastic material with external UV protection film) equipped with a pressure operating pump, fitted with a dispensing erogator (of variable type and shape) which enables the patient to direct the delivered solution within the oral cavity or on the tongue.

The dispensing system for oral use, and for topical use as well, shall primarily preserve melatonin from light and from oxidation (photodegradation and oxidation are the most common source of degradation in current commercial products containing melatonin) [Andrisano et al, 2000][88], in order to ensure a stability period from the production date up to a 24 months or even more storage period, and also to provide the most suitable dispensing system in relation to the intended dosage and site of application. Therefore, special nebulizers such as those based on airless technology dosing pumps, currently available in the market, equipped with nozzle or throat dispenser or based on bag on valve technology, equipped with a suitable dispenser, are those preferred as delivery systems for the diluted solution of the invention. The dosing pumps are also very suitable to accurately and precisely deliver the quantity of melatonin of the diluted solution, whenever intended for oral dose. The pharmaceutical dosage form based on the diluted solution, as defined above, can be distributed in a container with a volume ranging from 5 to 100 ml, preferably from 10 to 20 ml. An additional object is to provide pharmaceutical compositions as above and further described useful for the above purposes. These and other objects will be readily apparent to the ordinary artisan from consideration of the invention as a whole.

These Examples hereby are provided with the aim of better illustrating the invention and thus do not constitute any limitation of the invention itself, it being obvious that the spirit and scope of the invention also include any other modifications which are obvious to the person skilled in the art.

EXAMPLES

Example 1

Preparation of 400 ml Bulk Solution of Melatonin 10% (100 mg/1 Ml) and Filling of 2.0 ml Tubes and 5.0 ml Vials (Sterile).

Materials:
MLT (assay 99.1%) commercial batch n. J94343002;
Polyoxyl 40 hydrogenated castor oil commercial batch n. J6142004;
Ethanol (96 percent) commercially available batch n. BCBK8586.

Sterile glassware as necessary; materials and containers were from qualified manufacturers and additionally tested by the quality control. Quantities were reported to 100% assay. Cleanroom B equipped with aseptic laminar flow hood was used (temperature 21° C.; lightening system with UV filters).

Step 1—40.36 g MLT and 40.0 g polyoxyl 40 hydrogenated castor oil, both accurately weighed with a precision balance, were placed in a laboratory scale stainless steel mixer and thoroughly kneaded to yield an homogeneous pasty mass (about 15 minutes);

Step 2—400.0 ml of ethanol 96% were added to pasty mass inside the mixer (under vacuum and using nitrogen as a purge gas) and stirred slowly to complete dissolution while a clear and transparent solution was obtained (about 15 minutes). The resulting bulk solution was placed into a 500 ml amber glass bottle that was well closed with a suitable stopper, protected from light; about 370 ml of bulk solution were obtained (yield 92.5%).

Step 3—3.0 ml sample of the bulk solution withdrawn from the bottle with suitable pipette was sent to the laboratory for analysis (MLT assay).

Step 4—Once the bulk solution has received approval (assay melatonin 100.2 mg/1 ml), the bulk solution was passed through a sterilizing membrane filter and the filtered solution was collected in a closed glass bottle; the sterile solution was suitably apportioned under aseptic laminar flow hood (nitrogen was used as a process purge gas) according to the following filling program:

n. 70 test tubes from glass Type I (Ph. Eur.) were filled with 2.0 ml bulk solution and were closed with polypropylene stoppers, labelled and wrapped with aluminium film and placed in a dark box protected from light;

n. 40 glass sterile vials (10 ml capacity) Type I (Ph. Eur.) were filled with 5.0 ml portion of bulk solution, closed with stopper, firmly sealed with an aluminium capsule, labelled and placed in a dark box protected from light.

One sample of each strength (tube and vial) were sent to quality control; solutions passed physico-chemical tests (clear and transparent), melatonin assay (99.7 mg/ml), complied with pH range (6.5-7.5) and filled volume, with test for sterility and bacterial endotoxins (cumulative yield 85%). The released containers were partially used for the programmed stability tests Example 2

Preparation of 200 ml Bulk Solution of Melatonin 10% (100 mg/1 ml) and Aseptic Filling of 1.0 ml Bulk Solution into Amber Glass Ampoules.
Materials:
 MLT (assay 99.1%) commercial batch n. J94343002;
 Polyoxyl 15 hydroxystearate commercial batch n. 10063047G0;
 Ethanol (96 percent) commercial batch n. BCBK8586V.
 Sterile glassware as necessary; materials and containers were from qualified manufacturers and additionally tested by the quality control.
 All quantities were reported to 100% assay.
 Cleanroom B and Cleanroom A equipped with ampoules filling machine with filling station under laminar flow (temperature 21° C.; lightening system with UV filters; antideflagrant area and equipment).
 Step 1—20.18 g MLT and 20.0 g macrogol 15 hydroxystearate, both accurately weighed with a precision balance, were placed into a laboratory scale stainless steel mixer and thoroughly kneaded to yield an homogeneous pasty mass (about 15 minutes);
 Step 2—200.0 ml of ethanol (96 percent) were added to the pasty mass inside the mixer (under vacuum and using nitrogen as a purge gas) and stirred slowly to complete dissolution while a clear and transparent solution was obtained (about 15 minutes). The resulting bulk solution was placed into a 250 ml amber glass bottle that was well closed with a suitable stopper, protected from light (about 175 ml; steps yield 87.5%).
 Step 3—3.0 ml sample of the bulk solution withdrawn from the bottle with a suitable pipette was sent to the laboratory for analysis (MLT assay).
 Step 4—Once the bulk solution received the approval (assay melatonin 99.7 mg/1 ml), the bulk solution was passed through a sterilizing membrane filter and the filtered solution was collected directly into a glass bottle. The glass bottle with the sterile solution was passed into the Cleanroom A, where the bulk solution was apportioned by means of a filling machine into sterile amber glass ampoules (1.5 ml capacity) from glass Type I (Ph. Eur.). 128 amber glass ampoules were filled with 1.0 ml bulk solution; ampoules were automatically sealed by the machine, placed on plastic blisters and were transferred into a dark box protected from light.
 Two ampoules were sent to quality control; solutions passed physico-chemical tests (clear and transparent), melatonin assay (99.3 mg/ml), complied with pH range (6.5-7.5) and filled volume, with test for and sterility and bacterial endotoxins. The released product (n. 126 ampoules; cumulative yield 63%) was partially used for the programmed stability tests.

Example 3

Preparation of 500 Glass Ampoules of 1.0 ml Sterile Bulk Solution (100 Mg Melatonin/1 ml) from 500 ml Bulk Solution of Melatonin 10%.
Materials:
 MLTEP (assay 100.4%) commercial batch n. 140003;
 Polyoxyl 40 hydrogenated castor oil commercial batch n. 23660956P0;
 Anhydrous ethanol commercial batch n. C1311142.
 Sterile glassware as necessary; materials and containers were from qualified manufacturers and additionally tested by the quality control.
 All quantities were reported to 100% assay.
 Cleanroom B and Cleanroom A equipped with ampoules filling machine with filling station under laminar flow (temperature 21° C.; lightening system with UV filters).
 Step 1—49.80 g MLTEP (100.4%) and 50.0 g polyoxyl 40 hydrogenated castor oil, both accurately weighed with a precision balance, were placed in a laboratory scale stainless steel mixer and thoroughly kneaded to yield an homogeneous pasty mass (about 15 minutes);
 Step 2—500.0 ml of anhydrous ethanol were added to the pasty mass inside the mixer (before under vacuum and then using nitrogen as a purge gas) and stirred slowly to complete dissolution until a clear and transparent solution was obtained (about 15 minutes). The resulting bulk solution was placed into a 750 ml amber glass bottle that was well closed with a suitable stopper and protected from light (about 465 ml; yield 93%).
 Step 3—3.0 ml sample of the bulk solution withdrawn from the bottle with a suitable pipette was sent to the laboratory for analysis (MLTEP assay).
 Step 4—Once the bulk solution received the approval (assay melatonin 99.9 mg/1 ml), the bulk solution was passed through a sterilizing membrane filter and the filtered solution was collected directly into a glass bottle. The glass bottle with the sterile solution was passed into the Cleanroom A where the bulk solution was apportioned by means of a filling machine (under nitrogen laminar flow) into amber glass ampoules (1.5 ml capacity) from glass Type I (Ph. Eur.). A total 403 amber glass ampoules were filled with 1.0 ml bulk solution; ampoules were automatically sealed by the machine, placed on plastic blisters and were transferred into a dark box protected from light.
 Two ampoules were sent to quality control; solutions passed physico-chemical tests (clear and transparent), melatonin assay (99.6 mg/ml), complied with pH range (6.5-7.5) and filled volume, with the test for sterility and bacterial endotoxins. The released containers (n. 401 ampoules; cumulative yield 80.2%) were partially used for the programmed stability tests.

Example 4

Preparation of 1000 Glass Vials of 5.0 ml Sterile Bulk Solution of Melatonin 10% (100 mg Melatonin/1 ml).
Materials:
 MLTEP (assay 100.4%) commercial batch n. 140003;
 Polyoxyl 15 hydrogenated castor oil commercial batch n. 659832970V0;
 Ethanol 96% sterile commercial batch n. 14073-02.
 Sterile glassware as necessary; materials and containers were from qualified manufacturers and additionally tested by the quality control. All materials are from qualified manufacturers and have been previously tested by the quality control.
 Cleanroom B and Cleanroom A equipped with machine with filling station under laminar flow (temperature 21° C.; lightening system with UV filters).
 Step 1—498.00 g MLTEP (100.4%) and 500.0 g polyoxyl 15 hydrogenated castor oil, both accurately weighed with a precision balance, are placed in a laboratory scale stainless steel mixer and thoroughly kneaded to yield an homogeneous pasty mass (about 20 minutes);

Step 2—5000.0 ml of ethanol 96% sterile were added to pasty mass inside the mixer (before under vacuum and then using nitrogen as a purge gas) and stirred slowly to complete dissolution until a clear and transparent solution was obtained (about 20 minutes). The resulting bulk solution was placed into a 10 lt amber glass bottle that is well closed with a suitable stopper and protected from light (about 4820 ml; step yield 96.4%).

Step 3—About 3.0 ml sample of the bulk solution withdrawn from the bottle with a suitable pipette was sent to the laboratory for analysis (MLTEP assay).

Step 4—Once the bulk solution has received approval (assay melatonin 99.9 mg/ml), the bulk solution was passed through a sterilizing membrane filter and the filtered solution was collected directly into a ambered glass bottle. The glass bottle with the sterile solution was passed in the Cleanroom A where the bulk solution was apportioned by means of filling machine under nitrogen laminar flow into vial (10 ml capacity) from glass Type I (Ph. Eur.). A total 958 glass vials were filled with 5.0 ml bulk solution; vials were automatically closed with neoprene perforable stopper and fixed to the vial with an aluminium capsule. Vials were labelled and transferred into a dark box protected from light.

One vial was sent to quality control; solution passed physico-chemical tests (clear and transparent), melatonin assay (100.2 mg/ml), complied with pH range (6.5-7.5) and filled volume, with tests for sterility and bacterial endotoxins. The released product: n. 955 vials cumulative yield 99.5%. Some vials were partially used for the programmed stability tests.

Example 5

Specifications Characterizing the Pharmacy and Industrial Bulk Solution Package of Melatonin 10% for i.v. Use of the Invention.

Hereby listed the specifications characterizing the unit package of melatonin 10% solution for i.v. administration, being the 10% concentration of melatonin in the solution and the solution physiological range of pH between 6.0-7.5 the most typical parameters.

| Tests | Methods | Specifications |
|---|---|---|
| 1. Appearance | Visual control | Free of foreign particles |
| 2. Clarity | Ph. Eur. 2.2.1 | Clear solution |
| 3. Colour | Ph. Eur. 2.2.2 | Colourless solution |
| 4. Extractable volume | Ph. Eur. 2.9.17 | 100-105% of declared volume |
| 5. pH | Ph. Eur. 2.2.3 | 6.0-7.5 |
| 6. Related Substances | BP | |
| 5-methoxytryptamine | | ≤0.5% |
| each unknown impurity | | ≤0.1% |
| Total related substances | | ≤1.0% |
| 7. Microbiology | Ph. Eur. 2.6.1 | Sterile |
| 8. Endotoxins | Ph. Eur. 2.6.14 | ≤30 E.U./ml |
| 9. Assay LC (melatonin 10% = 100 mg/ml) | BP | 95.0-105.0% of declared content |

Ph. Eur. = European Pharmacopoeia current Edition
BP = British Pharmacopoeia current Edition Example 6

Stability Studies of Pharmacy and Industrial Bulk Solution Package of Melatonin 10% i.v. Use of the Invention.
Study Protocol
  Pharmaceutical form: 1.0 ml amber glass ampoule
  Batch no.: ampoules from Example 2
(A) Type of Stability: Accelerated
  Conditions: 40° C.±2° C./R.H. 75%±5% (climatic monitored storage)
  Duration: 6 months
  Intervals: 0 (initial), 3 and 6 months.

| Tests | Specifications | Time 0 | 3 months | 6 months |
|---|---|---|---|---|
| 1. Appearance | Free of particles | conform | conform | conform |
| 2. Clarity | Clear solution | clear | clear | clear |
| 3. Colour | Colourless | colourless | colourless | slightly opalescent |
| 4. Extractable volume | 1.0 ml (100-105%) | 103% | — | — |
| 5. pH | 6.0-7.5 | 6.9 | 6.8 | 7.1 |
| 6. Related Substances | | | | |
| 5-methoxytryptamine | ≤0.5% | <0.5% | <0.5% | 0.4% |
| each unknown impurity | ≤0.1% | <0.1% | <0.1% | 0.2% |
| Total related substances | ≤1.0% | <1.0% | <1.0% | 0.6% |
| 7. Microbiology | Sterile | sterile complies | — | — |
| 8. Endotoxins | ≤30 E.U./ml | | | |
| 9. Assay LC (melatonin) | 95.0-105.0% | 99.3% | 99.6% | 98.9% |

(B) Type of Stability: Long Term
  Conditions: 25° C.±2° C./R.H. 60%±5% (climatic monitored storage)
  Duration: 12 months
  Intervals: 0 (initial), 3, 6, 9 and 12 months (ongoing over 12 months)

| Tests | Specifications | Time 0 | 3 months | 6 months | 9 months | 12 months |
|---|---|---|---|---|---|---|
| 1. Appearance | Free of particles | conform | conform | conform | conform | conform |
| 2. Clarity | Clear solution | clear | clear | clear | clear | clear |
| 3. Colour | Colourless | colourless | colourless | colourless | colourless | colourless |
| 4. Extractable volume | 1.0 ml (100-105%) | 103% | — | — | — | — |
| 5. pH | 6.0-7.5 | 6.9 | 6.8 | 7.0 | 6.9 | 6.8 |

-continued

| Tests | Specifications | Time 0 | 3 months | 6 months | 9 months | 12 months |
|---|---|---|---|---|---|---|
| 6. Related Substances | | | | | | |
| 5-methoxytryptamine | ≤0.5% | <0.5% | <0.5% | <0.5% | <0.5% | <0.5% |
| each unknown impurity | ≤0.1% | <0.1% | <0.1% | <0.1% | <0.1% | <0.1% |
| Total related substances | ≤1.0% | <1.0% | <1.0% | <1.0% | <1.0% | <1.0% |
| 7. Microbiology | Sterile | sterile | — | — | — | sterile |
| 8. Endotoxins | ≤30 E.U./ml | complies | — | — | — | — |
| 9. Assay LC (melatonin) | 95.0-105.0% | 99.3% | 99.2% | 99.4% | 99.0% | 99.1% |

(C) Type of Stability: Cryogenic Shock
  Conditions: −10° C.±2° C./R.H. 75%±5% (climatic monitored storage)
  Duration: 3 days
  Intervals: 0 (initial), day 2 and day 3

| Tests | Specifications | Time 0 | Day 2 | Day 3 |
|---|---|---|---|---|
| 1. Appearance | Free of particles | conform | conform | Partial white precipitate; it dissolves completely at room t° and with slight shaking |
| 2. Clarity | Clear solution | clear | clear | See appearance |
| 3. Colour | Colourless | colourless | colourless | colourless |
| 4. Extractable volume | 1.0 ml (100-105%) | 103% | — | — |
| 5. pH | 6.0-7.5 | 6.9 | — | — |
| 6. Related Substances | | | | |
| 5-methoxytryptamine | ≤0.5% | <0.5% | — | <0.5% |
| each unknown impurity | ≤0.1% | <0.1% | — | <0.1% |
| Total related substances | ≤1.0% | <1.0% | — | <1.0% |
| 7. Microbiology | Sterile | sterile | — | — |
| 8. Endotoxins | ≤30 E.U./ml | complies | — | — |
| 9. Assay LC (melatonin) | 95.0-105.0% | 99.3% | — | 99.5% |

Example 7

Stability Studies of Pharmacy and Industrial Bulk Solution Package of Melatonin 10% i.v. Use of the Invention—5.0 ml Multidose Vial Study Protocol
  Pharmaceutical form: 5.0 ml vial (multidose)
  Batch no.: vials from Example 4
(A) Type of Stability: Accelerated
  Conditions: 40° C.±2° C./R.H. 75%±5% (climatic monitored storage)
  Duration: 6 months
  Intervals: 0 (initial), 3 and 6 months.

| Tests | Specifications | Time 0 | 3 months | 6 months |
|---|---|---|---|---|
| 1. Appearance | Free of particles | conform | conform | conform |
| 2. Clarity | Clear solution | clear | clear | clear |
| 3. Colour | Colourless | courless | courless | off-white |
| 4. Extractable volume | 5.0 ml (100-105%) | 104% | — | — |
| 5. pH | 6.0-7.5 | 6.8 | 6.8 | 6.9 |
| 6. Related Substances | | | | |
| 5-methoxytryptamine | ≤0.5% | <0.5% | <0.5% | 0.5% |
| each unknown impurity | ≤0.1% | <0.1% | <0.1% | 0.3% |
| Total related substances | ≤1.0% | <1.0% | <1.0% | 0.8% |
| 7. Microbiology | Sterile | sterile | — | — |
| 8. Endotoxins | ≤30 E.U./ml | complies | — | — |
| 9. Assay LC (melatonin) | 95.0-105.0% | 100.2% | 99.9% | 99.1% |

(B) Type of Stability: Long Term
  Conditions: 25° C.±2° C./R.H. 60%±5% (climatic monitored storage)
  Duration: 12 months
  Intervals: 0 (initial), 3, 6, 9 and 12 months (ongoing over 12 months)

| Tests | Specifications | Time 0 | 3 months | 6 months | 9 months | 12 months |
|---|---|---|---|---|---|---|
| 1. Appearance | Free of particles | conform | conform | conform | conform | conform |
| 2. Clarity | Clear solution | clear | clear | clear | clear | clear |
| 3. Colour | Colourless | colourless | colourless | colourless | colourless | colourless |
| 4. Extractable volume | 5.0 ml (100-105%) | 104% | — | — | — | — |
| 5. pH | 6.0-7.5 | 6.8 | 7.0 | 6.9 | 6.8 | 6.9 |
| 6. Related Substances | | | | | | |
| 5-methoxytryptamine | ≤0.5% | <0.5% | <0.5% | <0.5% | <0.5% | <0.5% |
| each unknown impurity | ≤0.1% | <0.1% | <0.1% | <0.1% | <0.1% | <0.1% |
| Total related substances | ≤1.0% | <1.0% | <1.0% | <1.0% | <1.0% | <1.0% |
| 7. Microbiology | Sterile | sterile | — | — | — | sterile |
| 8. Endotoxins | ≤30 E.U./ml | complies | — | — | — | — |
| 9. Assay LC (melatonin) | 95.0-105.0% | 100.2% | 99.9% | 100.3% | 99.7% | 99.8% |

(C) Type of Stability: Cryogenic Shock
Conditions: −10° C.±2° C./R.H. 75%±5% (climatic monitored storage)
Duration: 3 days
Intervals: 0 (initial), day 2 and day 3

| Tests | Specifications | Time 0 | Day 2 | Day 3 |
|---|---|---|---|---|
| 1. Appearance | Free of particles | conform | conform | Partial white precipitate; it dissolves completely at room t° and with slight shaking |
| 2. Clarity | Clear solution | clear | clear | Not completely clear |
| 3. Colour | Colourless | colourless | colourless | colourless |
| 4. Extractable volume | 5.0 ml (100-105%) | 104% | — | — |
| 5. pH | 6.0-7.5 | 6.8 | — | — |
| 6. Related Substances | | | | |
| 5-methoxytryptamine | ≤0.5% | <0.5% | — | <0.5% |
| each unknown impurity | ≤0.1% | <0.1% | — | <0.1% |
| Total related substances | ≤1.0% | <1.0% | — | <1.0% |
| 7. Microbiology | Sterile | sterile | — | — |
| 8. Endotoxin | ≤30 E.U./ml | complies | — | — |
| 9. Assay LC (melatonin) | 95.0-105.0% | 100.2% | — | 99.7% |

(D) Type of Stability: In Use (Discontinued)
Conditions: 25° C.±2° C./R.H. 75%±5% (climatic monitored storage)
Duration: 8 days
Intervals: 4 withdrawals each at 2 days intervals

| Tests | Specifications | Time 0 | Day 2 | Day 4 | Day 6 | Day 8 |
|---|---|---|---|---|---|---|
| 1. Appearance | Free of particles | conform | conform | conform | conform | conform |
| 2. Clarity | Clear solution | clear | clear | clear | clear | clear |
| 3. Colour | Colourless | colourless | colourless | colourless | colourless | colourless |
| 4. Extractable volume | 5.0 ml (100-105%) | 104% | — | — | — | — |
| 5. pH | 6.0-7.5 | 6.8 | 6.7 | 6.9 | 6-7 | 6-8 |
| 6. Related Substances | | | | | | |
| 5-methoxytryptamine | ≤0.5% | <0.5% | . . . | <0.5% | — | <0.5% |
| each unknown impurity | ≤0.1% | <0.1% | — | <0.1% | — | <0.1% |
| Total related substances | ≤1.0% | <1.0% | — | <1.0% | — | <1.0% |
| 7. Microbiology | Sterile | sterile | — | | | sterile |
| 8. Endotoxins | ≤30 E.U./ml | complies | — | | | |
| 9. Assay LC (melatonin) | 95.0-105.0% | 100.2% | 99.8% | 99.3% | 99.7% | 99.1% |

Example 8

Preparation of 2000 ml of Oral Solution of Melatonin (25 mg MLT/Ml).

Materials:
MLT (assay 99.1%) commercial batch n. J94343002;
Polyoxyl 40 hydrogenated castor oil commercial batch n. 23660956P0;
Ethanol 96% commercial batch n. 14073-02.

Auxiliary Ingredients:
Glycerol (E422) commercial product: 10.0%;
Xylitol (E967) commercial product: 7.0%;
Sodium saccharinate (E054) commercial product: 0.15%;
Cherry essence commercial product: 4.0%;
Purified water commercial product.

Glassware as necessary; ingredients, container (38 ml amber glass bottle) and stopper are from qualified manufacturers and additionally tested by the quality control. All quantities are reported to 100% assay.

Cleanroom B equipped with dosing machine for bottles (temperature 21° C.; lightening system with UV filters).
Preparation of 500 ml of Bulk Solution (Solution A)

Step 1—50.45 g MLT (assay 99.1%) and 50.0 g polyoxyl 40 hydrogenated castor oil, both accurately weighed with a precision balance, were placed in a laboratory scale stainless steel mixer and thoroughly kneaded to yield an homogeneous pasty mass (about 15 minutes);

Step 2—500.0 ml of ethanol 96 percent were added to pasty mass inside the mixer (before under vacuum and then using nitrogen as a purge gas) and stirred slowly to complete dissolution while a clear and transparent solution is obtained (about 15 minutes). The resulting bulk solution is placed into a 3000 ml amber glass bottle that is well closed with a suitable stopper, protected from light (about 465 ml; step yield 93.0%).

Step 3—3.0 ml sample of the above bulk solution withdrawn from the bottle was sent to the laboratory for analysis (MLT assay: 98.8 mg/ml).

Step 4—Preparation of 1500 ml of auxiliary ingredients (Solution B) In a 5 liters laboratory stirring tank (stainless steel) the following auxiliary ingredients (calculated to yield 2000 ml final oral concentrated solution) glycerol 200 g, xylitol 140 g, sodium saccharinate 3.0 g were thoroughly mixed in 1500 ml purified water until complete dissolution.

Step 5—Preparation oral concentrated solution (theoretical 2000 ml). 465 ml bulk solution (melatonin assay correction factor of 98.8/100=459 ml of 100% melatonin) was placed into a laboratory stirring tank from stainless steel and the cherry essence (8.0 g) was firstly dissolved into bulk solution A and stirred to complete dissolution. Thereafter 1395 ml of bulk solution B (by weight), representing the 75% of the final solution, were added and admixed to yield the final volume of 1854.0 ml of oral concentrated solution.

Step 6—3.0 ml sample of the diluted solution withdrawn from the bottle was sent to the laboratory for analysis (MLT assay: 24.95 mg/ml).

Step 7—Once the oral concentrated solution received approval, it was passed through a membrane filter and the filtrate was collected directly into a suitable amber glass bottle. The bottle containing the diluted solution was passed to the Cleanroom B where the solution was apportioned by means of a dosing machine into amber glass bottles (38 ml capacity) from glass Type I (Ph. Eur.). A total 51 glass bottles filled with 30.0 ml diluted solution dosed at 25 mg MLT/ml were obtained; bottles were automatically closed by a suitable child proof anti-pilfer cap. The bottles were then labelled and transferred into a dark box protected from light.

Two complete bottles were sent to quality control; solution passed physico-chemical tests (clear and transparent), melatonin assay (24.90 mg/ml), complied with pH range (6.5-7.5), filling volume and with microbiological enumeration test (TAMC max $10^{-2}$ CFU/g; TYMC max 10 CFU/g). The product was packed in a folding box along with a dosing plastic device to adapt the solution dosage according to its use.

The released product (n. 49 bottles; cumulative yield 74%) were partially used for the programmed stability tests.

Example 9

Stability Studies of Pharmacy and Industrial Bulk Solution Package of Melatonin for Oral Use of Example 8 of the Invention—30.0 ml Multidose Bottle.
Study Protocol
Pharmaceutical form: 30.0 ml (25 mg MLT/ml) amber glass bottle (multidose)
Batch no.: bottle from Example 8
(A) Type of Stability: Accelerated
Conditions: 40° C.±2° C./R.H. 75%±5% (climatic monitored storage)
Duration: 6 months
Intervals: 0 (initial), 3 and 6 months.

| Tests | Specifications | Time 0 | 3 months | 6 months |
|---|---|---|---|---|
| 1. Appearance | Free of particles | conform | conform | conform |
| 2. Clarity | Clear solution | clear | clear | clear |
| 3. Colour | Colourless | colourless | colourless | colourless |
| 4. Mean volume (vial) | 30.0-31.5 ml | 31.2 ml | — | — |
| 5. pH | 6.0-7.5 | 6.9 | 7.0 | 6.9 |
| 6. Related Substances | | | | |
| 5-methoxytryptamine | ≤0.5% | <0.5% | <0.5% | 0.3% |
| each unknown impurity | ≤0.1% | <0.1% | <0.1% | 0.2% |
| Total related substances | ≤1.0% | <1.0% | <1.0% | 0.5% |
| 7. Microbiology (CFU/g) | | | | |
| TAMC | ≤$10^{-2}$ | ≤$10^{-2}$ | — | ≤$10^{-2}$ |
| TYMC | ≤10 | ≤10 | — | ≤10 |
| 8. Assay LC (melatonin) | 95.0-105.0% | 99.7% | 99.3% | 99.2% |

(B) Type of Stability: Long Term
Conditions: 25° C.±2° C./R.H. 60%±5% (climatic monitored storage)
Duration: 12 months
Intervals: 0 (initial), 3, 6, 9 and 12 months (ongoing over 12 months)

| Tests | Specifications | Time 0 | 3 months | 6 months | 9 months | 12 months |
|---|---|---|---|---|---|---|
| 1. Appearance | Free of particles | conform | conform | conform | conform | conform |
| 2. Clarity | Clear solution | clear | clear | clear | clear | clear |
| 3. Colour | Colourless | colourless | colourless | colourless | colourless | colourless |
| 4. Mean volume (vial) | 30.0-31.5 ml | 31.2 ml | — | — | — | — |
| 5. pH | 6.0-7.5 | 6.9 | 7.0 | 6.8 | 7.1 | 6.9 |

| Tests | Specifications | Time 0 | 3 months | 6 months | 9 months | 12 months |
|---|---|---|---|---|---|---|
| 6. Related substances | | | | | | |
| 5-methoxytryptamine | ≤0.5% | <0.5% | <0.5% | <0.5% | <0.5% | <0.5% |
| each unknown impurity | ≤0.1% | <0.1% | <0.1% | <0.1% | <0.1% | <0.1% |
| Total related substance | ≤1.0% | <1.0% | <1.0% | <1.0% | <1.0% | <1.0% |
| 7. Microbiology (CFU/g) | | | | | | |
| TAMC | ≤$10^{-2}$ | ≤$10^{-2}$ | — | — | — | ≤$10^{-2}$ |
| TYMC | ≤10 | ≤10 | — | — | — | ≤10 |
| 8. Assay LC (melatonin) | 95.0-105.0% | 99.7% | 100.2% | 99.6% | 99.1% | 99.4% |

(C) Type of Stability: In Use (Continued)
  Conditions: 25° C.±2° C./R.H. 75%±5% (climatic monitored storage)
  Duration: 30 days
  Withdrawal: 1 ml once a day
  Intervals: analysis at the end of each week

| Tests | Specifications | Time 0 | Week 1 | Week 2 | Week 3 | Week 4 |
|---|---|---|---|---|---|---|
| 1. Appearance | Free of particles | conform | conform | conform | conform | conform |
| 2. Limpidezza | Clear solution | clear | clear | clear | clear | clear |
| 3. Colour | Colourless | colourless | colourless | colourless | colourless | colourless |
| 4. Mean volume (vial) | 30.0-31.5 ml | 31.2 ml | — | — | — | — |
| 5. pH | 6.0-7.5 | 6.9 | 6.8 | 7.0 | 6.9 | 7.1 |
| 6. Related substances | | | | | | |
| 5-methoxytryptamine | ≤0.5% | <0.5% | — | — | — | <0.5% |
| each unknown impurity | ≤0.1% | <0.1% | — | — | — | <0.1% |
| Total related substance | ≤1.0% | <1.0% | — | — | — | <1.0% |
| 7. Microbiology (CFU/g) | | | | | | |
| TAMC | ≤$10^{-2}$ | ≤$10^{-2}$ | — | — | — | ≤$10^{-2}$ |
| TYMC | ≤10 | ≤10 | — | — | — | ≤10 |
| 8. Assay LC (melatonin) | 95.0-105.0% | 99.7% | 100.1% | 99.6% | 99.2% | 98.7% |

Example 10

Instant Preparation of 10 Bottles by 500 ml of Sodium Chloride Intravenous Infusion (Diluted Solution of Melatonin 0.2 mg/1 ml)
Materials:
  n. 10 glass ampoules (100 mg/1.0 ml) from Example 3;
  n. 10 commercial bottles by 500 ml Sodium Chloride Intravenous Infusion.
  Sterile disposable syringes (2 ml capacity)
  Vertical laminar flow safety hood (temperature 21° C.; lightening system with UV filters).
  Step 1—The operator passed accurately a damp cloth with ethanol around the container of each of the 10 commercial bottles of Sodium Chloride Intravenous Infusions and placed them into the laminar flow safety hood where the plastic protection seals was opened and removed.
  Step 2—Each glass ampoule of bulk solution (100 mg melatonin/1 ml) from Example 3 was opened one by one, the liquid was independently withdrawn from each glass ampoule by means of the disposable syringe and the needle was used to perforate the rubber stopper of each bottle of Sodium Chloride to inject inside the bottle the bulk solution withdrawn from each ampoule. A small portion (about 1 ml) of the Sodium Chloride infusion was aspirated and re-injected again in order to recover the bulk solution from the cylinder and piston of the syringe. The syringe was then definitely extracted from the rubber stopper and disposed, while the plastic protection cover was re-installed by pressure on the glass bottle and the prepared diluted solution.

One 500 ml infusion bottle was sent to quality control; diluted solution passed physico-chemical tests (clear and transparent), melatonin assay (1.02 mg/ml), complied with pH range (6.5-7.5) and with tests for sterility and bacterial endotoxins.

The released product (n. 9 vials; cumulative yield 90%) was partially used for the programmed pharmacokinetic study.

Example 11

Preparation of 200 Spray Bottles (15.0 ml Diluted Solution 10 mg/ml-1 mg MLT/0.1 ml Actuation) from Bulk Solution of Melatonin 10%.
Materials:
  MLT (assay 99.1%) commercial batch n. J94343002;
  Polyoxyl 40 hydrogenated castor oil commercial batch n. 23660956P0;
  Ethanol 96 percent commercial batch n. 14073-02.
Auxiliary Ingredients:
  Glycerol (E422) commercial product; quantity: 10.0%;
  Xylitol (E967) commercial product; quantity: 7.0%;
  Sodium saccharinate (E054) commercial product; quantity: 0.15%;
  Mint essence commercial product; quantity: 4.0%;
  Purified water in house production.
  Glassware as necessary; materials (pump dosing 0.1 ml and actuator), ingredients and containers (17 ml glass bottle) are from qualified manufacturers and additionally tested by the quality control. All quantities are reported to 100% assay.

Cleanroom B equipped with dosing machine for bottles (17 ml capacity bottle cooperating with 0.1 ml dosing pump with oral applicator) (temperature 21° C.; lightening system with UV filters).

Preparation of 300 ml of Bulk Solution (Solution A)

Step 1—30.27 g MLT (assay 99.1%) and 30.0 g polyoxyl 40 hydrogenated castor oil, both accurately weighed with a precision balance, were placed in a laboratory scale stainless steel mixer and thoroughly kneaded to yield an homogeneous pasty mass (about 15 minutes);

Step 2—300.0 ml of ethanol 96 percent were added to pasty mass inside the mixer (before under vacuum and then using nitrogen as a purge gas) and stirred slowly to complete dissolution while a clear and transparent solution is obtained (about 15 minutes). The resulting bulk solution is placed into a 500 ml amber glass bottle that is well closed with a suitable stopper, protected from light (about 275 ml; step yield 91.6%).

Step 3—3.0 ml sample of the bulk solution withdrawn from the bottle was sent to the laboratory for analysis (MLT assay: 98.7 mg/ml).

Step 4—Preparation of 2400 ml of auxiliary ingredients (Solution B) In a 5 liters laboratory stirring tank (stainless steel) the following auxiliary ingredients glycerol 270 g, xylitol 189 g, sodium saccharinate 4.0 g were thoroughly mixed in 2400 ml purified water until complete dissolution.

Step 5—Preparation of diluted solution (theoretical 2665 ml).

270 ml bulk solution (melatonin assay correction factor of 98.7/100) was placed into a laboratory stirring tank from stainless steel and the mint essence (9.6 g) was firstly dissolved into bulk solution A and stirred to complete dissolution. Thereafter 2395 ml of bulk solution B (by weight, representing the 90% of the corrected solution A) were added and admixed to yield the final volume of 2665.0 ml of diluted solution.

Step 6—3.0 ml sample of the diluted solution withdrawn from the bottle was sent to the laboratory for analysis (MLT assay: 10.2 mg/ml).

Step 7—Once the bulk solution received approval, the solution was passed through a membrane filter and the filtered solution was collected directly into a suitable amber glass bottle. The bottle containing the diluted solution was passed to the Cleanroom B where the solution was apportioned by means of a filling machine into amber glass bottles (17 ml capacity) from glass Type I (Ph. Eur.). A total 152 glass bottles filled with 15.0 ml diluted solution were obtained; bottle were automatically closed by crimping the dosing pump on the bottle neck and the cooperating oral actuator was also installed on the pump steam. The bottles were labelled and transferred into a dark box protected from light.

Two complete bottles were sent to quality control; solution passed physico-chemical tests (clear and transparent), melatonin assay (10.7 mg/ml), complied with pH range (6.5-7.5), filling volume and with microbiological enumeration test (TAMC max $10^{-2}$ CFU/g; TYMC max 10 CFU/g); functions and dosing of the complete device were approved as well.

The released product (n. 150 spray bottles; cumulative yield 75%) were partially used for the programmed stability tests.

Example 12

Preparation of 200 Spray Bottles (10.0 ml Diluted Solution/Dosing 3 Mg MLT/0.2 ml Puff) from Bulk Solution of Melatonin 10%.

By operating in accordance to the procedures described in the previous Example 11 the following products and quantities were used to yield 100 ml of diluted solution of melatonin 1.5 mg/0.1 ml.

Materials:
MLTEP (assay 100.4%) commercial batch n. 140003;
Polyoxyl 15 hydroxystearate commercial batch n. 10063047G0;
Ethanol 96 percent commercial batch n. 14073-02.

Auxiliary Ingredients:
Glycerol (E422) commercial product; quantity: 10.0%;
Xylitol (E967) commercial product; quantity: 7.0%;
Neohesperidin DC (E959) commercial product; quantity: 0.05%;
Strawberry essence commercial product; quantity: 4.0%;
Purified water in house production.

Glassware as necessary; materials (pump dosing 0.2 ml and actuator), ingredients and containers (17 ml glass bottle) are from qualified manufacturers and additionally tested by the quality control. All quantities are reported to 100% assay.

Preparation of 300 ml of Bulk Solution (Solution A)

Step 1—30.0 g MLTEP (100.4%) and 30.0 g Polyoxyl 15 hydroxystearate,

Step 2—300.0 ml of ethanol 96 percent were used to yield 290 ml of bulk Solution A.

Step 3—bulk solution MLTEP assay: 100.5 mg/ml.

Preparation of 1720 ml of Auxiliary Ingredients (Solution B)

Used auxiliary ingredients glycerol 200 g, xylitol 140 g, neohesperidin DC 0.1 g were mixed in 1720 ml purified water.

Step 4—Preparation of diluted solution (theoretical 2000 ml).

The strawberry essence (8.0 g) was dissolved in 290 ml bulk solution A. 1710 ml (by weight) of solution B were slowly added and admixed to yield the final volume of 2000 ml of diluted solution.

Step 5—3.0 ml sample of the diluted solution withdrawn from the bottle was sent to the laboratory for analysis (MLT assay: 15.3 mg/ml).

Step 6—A total 149 glass bottles filled with 10.0 ml diluted solution were obtained.

Two complete glass bottles were sent to quality control; solution passed physico-chemical tests (clear and transparent), melatonin assay (15.2 mg/ml), complied with pH range (6.5-7.5), with filling volume and with microbiological enumeration test (TAMC max $10^{-2}$ CFU/g; TYMC max 10 CFU/g); functions and dosing of the complete device were approved as well. The released product (n. 147 spray bottles; cumulative yield 73%) were partially used for the programmed stability tests.

Example 13

Protective Effect of Melatonin in Mouse Model of EBOV Experimentally Induced Infection.

Foreword

Several animal models have been recently developed for EVD using non-human primates (NHPs) and rodents, which are crucial to understand pathophysiology and to develop diagnostics, vaccines, and therapeutics. Rhesus and cynomolgus macaques are representative models of filovirus infection as they exhibit remarkably similar symptoms to those observed in humans. However, the NHP models have practical and ethical problems that limit their experimental use. Furthermore, there are no inbred and genetically manipulated strains of NHP. Rodent models such as mouse, guinea pig, and hamster, have also been developed. However, these rodent models require adaptation of the virus to produce lethal disease and do not mirror all symptoms of human filovirus infection. Since melatonin is a biological response modifier (immunomodulator) leading also the endocrine system, in presence of altered conditions melatonin helps to activate, boosts or restore normal immune functions in mammals. Mechanism of action is multifaceted by working through the pineal-gut axis but also at the level of organ and cellular molecular MTs receptors and cascades, rather then by targeting viral protein or genetic sequences, so that the protective effects shall be evaluated in small animal models rather than in vitro cultures with a reduced or absent immunological response. However, an open study has been designed (without reference product), since there is no drug approved by any Health Authority for the treatment of EVD condition.

The advantage appears that the cellular antiviral pathways of innate immunity are not subject to the mutational changes characterizing EBOV, thus suggesting that, even in face of viral mutation, the natural modifier melatonin activating in any case the innate immunity, is likely to continue to show sustained biological activity of organ and cellular defence.

Materials and Methods
Drug and Doses

The solution of melatonin (Example 2 by oral route and Example 5 by i.v.) was suitably diluted and administered at different dose levels of melatonin (50, 100 and 150 mg/Kg/day) by i.v. (by using miniature infusion pump) or orally (by gavage), according to the known animals circadian cycle, at 30 minutes post-challenge and continuing for 15 days. A two days oral pretreatment before challenge was also performed at the two higher doses.

Animal Model

Studies were carried out in according to the international protocol in relation to code of practice for the housing and care of animal used in scientific procedure. Animals were given a week acclimatisation in the isolator biosafety level 4 (BSL-4) before entering the experiment to exclude any other ongoing pathology that could alter the experiment. The admitted animals (Bulb/c male, 9-10 weeks age) were divided in 9 groups of 6 mice each. One group (n.1) was used as absolute control (not challenged and non treated), while 8 groups of mice were infected at the same time by a single subcutaneous inoculation of 100 PFU of mouse-adapted Ebola virus (0.2 ml PBS). Survival for 16 days were monitored.

Study Design and Results

| Group | n. (*) | Treatment product | Dose mg/kg Body weight | Route Admin. | Duration after challenge (days) | Survival at day 16 |
|---|---|---|---|---|---|---|
| 1 | 6 | none | control | — | — | 6/6 |
| 2 | 6 | saline | saline | IV | 15 | 0/6 |
| 3 | 6 | MLT | 50 | IV | 15 | 4/6 |
| 4 | 6 | MLT | 100 | IV | 15 | 5/6 |
| 5 | 6 | MLT | 100 | OS | 15 | 5/6 |
| 6 | 6 | MLT | 100 | OS | P 2 + 15 | 6/6 |
| 7 | 6 | MLT | 150 | IV | 15 | 6/6 |
| 8 | 6 | MLT | 150 | OS | 15 | 6/6 |
| 9 | 6 | MLT | 150 | OS | P 2 + 15 | 6/6 |

(*) male 9-10 weeks age
P = Pretreatment (2 + 15 days)

Results

Survival has been considered as the parameter to monitor the protection effects of melatonin versus Ebola virus induced condition in the animal model. Partial beneficial effects were observed at the dose of 50 mg/Kg/day of melatonin. Complete survival against EBOV infection was experimentally achieved as from 100 mg/kg/day with 2 days oral pretreatment and in all other cases (IV and oral) at the dose regimen of 150 mg/Kg/day during the 15 days treatment. The above findings are the demonstration that the melatonin solution of the invention has elicited an adequate immunological response that produced the desired effectiveness and protection versus the induced infection. However, melatonin oral pretreatment as from 100 mg/Kg/day has demonstrated to improve consistently the survival rate, thus confirming the possibility to use the lower dose level of melatonin also for prophylactic use in health professionals and health-care workers resulting frequently infected while attending patients with suspected or confirmed EVD. Finally this study confirmed the known data that high dose regimen levels of melatonin ranging from 50 to 150 mg/Kg/day are absolutely well tolerated in mammals.

Example 14

Protective Effect of Melatonin in Mouse Model of Dengue Virus (DENV) Experimentally Induced Infection.

The development of animal models of Dengue virus (DENV) infection and disease has been challenging, as epidemic DENV does not naturally infect non-human species. Non-human primates (NHPs) can sustain viral replication in relevant cell types and develop a robust immune response, but they do not develop overt disease. In contrast, certain immunodeficient mouse models infected with mouse-adapted DENV strains show signs of severe disease similar to the 'vascular-leak' syndrome seen in severe Dengue in humans. Humanized mouse models can sustain DENV replication and show some signs of disease, but further development is needed to validate the immune response. Classically, immunocompetent mice infected with DENV do not manifest disease. However, a new model using high doses of DENV has recently been shown to develop hemorrhagic signs after infection. Overall, each model has its advantages and disadvantages and is differentially suited for studies of Dengue pathogenesis and immunopathogenesis and/or pre-clinical testing of antiviral drugs and vaccines.

Differently from antiviral drugs, melatonin, a biological response modifier, in presence of altered conditions helps to activate, boosts or restore normal immune functions in mammals, and the mechanism of action is multifaceted by working through the pineal-gut axis but also at the level of cellular molecular MTs receptors and cascades, rather then by targeting viral protein or genetic sequences, the protective effects shall be evaluated in small animal models, rather than in vitro cultures with a reduced or absent immunological response. However, an open study has been necessarily designed (without reference product), since no drug has been approved by any Health Authority for the treatment of Dengue.

Materials and Methods
Drug and Doses

Melatonin concentrated solution of the invention (Example 2 by i.v.) was suitably used after dilution and administered at two different high dose levels (75, 100 and 150 mg/Kg/day) by i.v. (by using miniature infusion pump) according to the animals circadian cycle, at 30 minutes post-challenge and continuing for 19 consecutive days.

Animal Model

Studies were carried out in according to the international protocol in relation to code of practice for the housing and care of animal used in scientific procedure. Animals were given a week acclimatisation before entering the experiment to exclude any other ongoing pathology that could alter the experiment. The admitted animals (AG129 mice male, 5-6 weeks age) were divided in 4 groups of 10 mice each. One group (n. 1) was used as control, while 3 groups of mice were infected at the same time by a single intraperitoneally (i.p.) inoculation of $10^5$ PFU of mouse-adapted DENV-2 strain D2S10. Survival for 20 days was monitored.

Study Design and Results

| Group | n. (*) | Treatment product | Dose mg/kg Body weight | Route Admin. | Treatment (days) after challenge | Survival at day 20 |
| --- | --- | --- | --- | --- | --- | --- |
| 1 | 10 | saline | saline | IV | 19 | 0/6 |
| 2 | 10 | MLT | 75 | IV | 19 | 4/6 |
| 3 | 10 | MLT | 100 | IV | 19 | 6/6 |
| 4 | 10 | MLT | 150 | IV | 19 | 6/6 |

(*) M/F 5-6 weeks age

Results

Survival has been considered as the parameter to monitor the protection effects of melatonin versus Dengue virus induced condition in the animal model. Partial beneficial effects were observed at the dose of 75 mg/Kg/day of melatonin. Complete survival against DENV infection was experimentally achieved both at the dose regimen of 100 and 150 mg/Kg/day during 19 days treatment. The above findings are the demonstration that melatonin solution of the invention has elicited an adequate immunological response that produced the desired effectiveness and protection versus the induced infection. Finally this study confirmed also the published data that high dose regimen levels of melatonin ranging from 75 to 150 mg/Kg/day are absolutely well tolerated in mammals.

BIBLIOGRAPHIC REFERENCES

[1] Yeleswaram K et al. J Pineal Res, 1997; 22:45-51
[2] Waldhauser F et al. Neuroendocrinology, 1984; 39:307-313.
[3] Shirakawa S et al. Psychiatry and clinical neur, 1998; 52:266-267.
[4] Fourtillan J B et al. Biopharm Drug Dispos, 2000; 21:15-22.
[5] Vakkuri 0 et al. Life Sciences, 1985; 37 (5):489-495.
[6] DeMuro R L et al. Journal of Clinical Pharmacology, 2000; 40:781-784.
[7] Kopin I J et al. Journal of Biological Chemistry, 1971; 236:3072-3075.
[8] Vitte P A et al. J Pineal Res, 1998; 5(5):437-453.
[9] Mallo C et al. European J of Clinical Pharm, 1990; 38:297-301.
[10] Le Bars D et al. Nuclear Medicine and Biology, 1991; 18(3), 357-362.
[11] Facciolá G et al. European J of Clinical Pharm, 2001; 56(12):881-888.
[12] Ma X et al. Drug Metabolism and Disposition, 2005; 33(4):489-494.
[13] Reiter E J et al. Polish Journal of Pharmacology, 2004; 56:159-170.
[14] Vijayalaxmi T C R Jr et al. J Clin Oncol, 2002; 20:2575-2601.
[15] Korkmaz A et al. Mol Med 2009; 15:43-50.
[16] Bonnefont-Rousselot D et al. Toxicology 2010; 278: 55-67.
[17] Megdal S P et al. Eur J Cancer, 2005; 41:2023-2032.
[18] Wettenberg L. Reprod Nutr Dev 1999; 39(3):367-382.
[19] Karamitri A et al. Mol Endocrinol, 2013 August; 27(8):1217-33.
[20] Glaser S et al. Hepatobiliary Surg Nutr, 2104 Feb. 3; 3(1):35-43.
[21] Reiter R J et al. Hum Reprod Update 2014 March-April; 20(2):293-307.
[22] Tordjman S et al. Int J Mol Sci. October 2013; 14(10): 20508.20542.
[23] Lin L et al. Int J Mol Sci, 2013 July; 14(7):14574-93.
[24] Wade A G et al. Clinical Investigations in Aging, 2014 June; 9:947-961.
[25] Coto-Montes A et al. Mol Cell Endocrinol 2012 Sep. 25; 361(1-2):12-13.
[26] Suzuki K et al. Parkinson's Disease, 2011, Article ID 219056, 10 pages.
[27] Dowling G A et al. Sleep Med, 2005 September; 6(5):459-66.
[28] Srinivasan V et al. Ther Adv Neurol Disord, 2011; 4(5):297-317.
[29] Sterniczuk R et al. Clinical Interventions in Ageing, 2014; 9:969-977.
[30] Adamczyk-Sowa M et al. Nuerochem Res, 2014; 39:1585-1593.
[31] Kinnukan J A et al. Gastroenterol Hepatol (NY), 2013; 9(11):718-727.
[32] Gitto E et al. Pediatr Res, 2001; 50:756-760.
[33] Sahib A S et al. Ann Burns Fire Disasters, 2010; 23:199-205.
[34] Dominguez-Rodriguez A et al. Contemp Clin Trials, 2007; 28:532-539.
[35] Caumo W et al J Pain, 2009; 10:100-108.
[36] Borazan H et al. J Anesth, 2010; 24:155 160.
[37] Gitto E et al. J Pediatr Surg, 2004; 39:184-189.
[38] Jarratt J et al. Anaesth Intensive Care, 2011 March; 39(2):171-81.
[39] Maitra S et al. Saudi J Anaesth, July-September 2013; 7(3):315-321.
[40] Wang Y M et al. Cancer Chemother Pharm, 2012 May; 69(5):1213-20.
[41] Seely D et a. Integr Cancer Ther, 2012 December; 11(4):293-303.
[42] Ghielmini M et al. British Journal of Cancer, 1999; 80(7):1058-1061.
[43] Bennekul K et al. World J Hepatol, Apr. 27, 2014; 6(4):230-242.
[44] Martín V et al. British J Cancer, 2013; 108:2005-2012.
[45] Carrillo-Vico A et al. Int J Mol Sci, 2013; 14:8638-8683.
[46] Aversa S et al. J Matern Fetal Neonatal Med, 2012; 25:207-221.
[47] Ismail S A et al. Anesth Analg, 2009; 108:1146 1151.
[48] Berk L et al. Int J Radiation Oncology Biol Phys, 2007; 68:852 857.
[49] Gitto E et al. Oxidative Medicine and Cell Longevity, 2013, ID 980374.
[50] Alonso-Alconada D et al. Int J Mol Sci, 2013, 14, 9379-9395.
[51] Lane E A et al. J Clin Endocrinol Met, 1985; 61(6): 1214-6.
[52] Bagci S et al. Paediatr Crit Care Med, 2012 March; 13(2):e120-3.

[53] Moroni B et al Critical Care, 2010, 14(Suppl 1):p 494 (30th Int Symp on Int Care and Em Med., Brussels 9-12 Mar. 2010).
[54] Alan K et al. Critical Care 2010, 14(Suppl 1):p 39 (30th Int Symp on Int Care and Em Med., Brussels 9-12 Mar. 2010).
[55] Srinivasan V et al. J Crit Care 2012 December; 25(4): 656.e1-6.
[56] Galley H et al. J Pineal Res, 2014; 56:427-438.
[57] Shinozuka K et al. Int J Mol Sci, 2013, 14, 8924-8947.
[58] Manev H et al. FASEB J, 1996; 10(13):1546-1551.
[59] Kilic E et al. J. Cereb. Blood Flow Metab, 1999 May, 19, 511-516.
[60] Pei Z et al. Stroke, 2003; 34:770-775.
[61] Sinha K et al. Eur J Pharmacol, 2001; 428:185-192.
[62] Lee E J et al. J Pineal Res, 2005; 38:42-52.
[63] Lee M Y et al. J Pineal Res, 2007; 42:297-309.
[64] Kondoh T et al. Life Sci, 2002; 72:583-590.
[65] Chen T Y, et al. J. Pineal Res, 2006; 40:242-250.
[66] Kilic E et al. J. Pineal Res. 2008, 45, 142-148.
[67] Brzezinski. N. Engl J Med, 1997; 336:186-195.
[68] Pei Z et al. Neurosci Lett, 2002; 318:141-144.
[69] Pei Z et al. J Pineal Res, 2002; 32:168-172.
[70] Borlongan C V et al. FASEB J, 2000; 14:1307-17.
[71] Reiter R J et al. Exp Biot Med, 2005; 230:104-117.
[72] Generali J A et al. Hosp Pharm, 2013; 48(5):378-379.
[73] Wilhelmsen M et al. J Pineal Res, 2011 October; 51(3):270-7.
[74] Azevedo de Zanette S et al. BMC Pharm and Toxicology, 2014; 15:40.
[75] Kurdl M S et al. Indian J of Anaesthesia, March-April-2013; 57(2):133-144.
[76] Holley J L et al. Am J Kidney Dis, 1992 February; 19(2):156-61.
[77] Walker S et al. Am J Kidney Dis, 1995 November; 26(5):751-6.
[78] Masaumi M et al. Int J Prev Med, 2013 February; 4(2); 165-172.
[79] Koch B C et al. Am J Kidney Dis, 2009; 53:658-64.
[80] Russcher M, et al. Frontiers in Bioscience, 2012 Jun. 1; 17:2644-2656.
[81] Sharma U. Indian J Nephrol, 2013 July-August; 23(4): 269-270.
[82] Aperis G et al. J Ren Care, 2012 June; 38(2): 86-92.
[83] Edalat-Nejad M. et al. Indian J Nephrol, 2013 July-August; 23(4):264-269.
[84] Jaworek J et al. Histol Histopathol, 2014; 29:423-431.
[85] Katkar G D et al. J Pineal Res, 2014; 56:295-312.
[86] Shida C S et al. J Pin Res, 1994; 16:198-201.
[87] Kandimalla K K et al. J Control Release, 1999; 61:71-82.
[88] Andrisano V eta al. J Pharm Biomed Anal, 2000; 23:15-23.
[89] Daya S et al. J Pineal Res, 2001; 31:155-158.
[90] Dayal P P et al. AAPS Pharm Sci, 2003; 5:T3017.
[91] Lee B J et al. Arch Pharm Res, 1997; 20:560-565.
[92] Lee B J et al. Arch Pharm Res, 1998; 2:503-507.
[93] Cavallo A et al. J Pineal Res, 1995, 18(2), 90-92.
[94] Cheung R T et al. Journal of Pineal Research, 2006 November; 41(4):337-43.
[95] Malow B A et al. J Autism Dev Disord 2012; 42(8): 1729-37.
[96] Humphreys J S et al. Arch Dis Child 2014; 99:114-118.

The invention claimed is:

1. A pharmaceutical formulation of a concentrated bulk solution and of a pharmacy or industrial bulk package composition consisting of liquid preparation of melatonin comprising:
   melatonin (MLT);
   a polyethoxylated derivative (PED) selected from the group consisting of: macrogolglycerol hydroxystearate, macrogolglycerol ricinoleate, macrogol 15 hydroxystearate, and mixtures thereof; and
   ethanol, present in a volumetric amount sufficient to provide up to 100 mg melatonin per ml of solution (10% w/v);
   wherein the liquid formulation of melatonin, concentrated up to 10%, is present as a pharmacy or industrial bulk package; and
   wherein the weight ratio of melatonin to PED is in the range of from 0.90:1.1 to 1.1:0.90.

2. The pharmaceutical formulation of claim 1 further characterized that the preferred optimal ratio of MLT/PED/Ethanol in the bulk solution is 1.0:1.0:10 (w/w/v), with individual and relative variations comprised from about 90% to about 110% for each ingredient.

3. The pharmaceutical formulation of claim 1, wherein:
   the melatonin is Melatonin Extra-Pure (MLTEP), present in the bulk solution at the exact concentration of 10.0% weight/volume;
   the PED is selected from: macrogolglycerol hydroxystearate (polyoxyl 40 hydrogenated castor oil), with restriction of the nominal value to 40-45, and macrogol 15 hydroxystearate (polyoxyl 15 hydroxystearate), with nominal value 15; and
   the ethanol is has a purity of at least that of Ethanol (96 percent).

4. The pharmaceutical formulation of claim 3, wherein the MLTEP has a purity content in the range of from 99.0% to 101.0%, calculated on the dry basis, complies with the endotoxins requirement of max 300 I.U./gram, and with microbiological enumeration test for total aerobic microbial count ("TAMC") max $10^{-2}$ CFU/g and total combined yeasts and moulds count ("TYMC") max 10 CFU/g.

5. The pharmaceutical formulation of claim 3, wherein MLTEP is present at the precise concentration of 10.0% weight/volume of the bulk solution, such that 1.0 ml of the bulk solution contains exactly 100 mg of MLTEP.

6. A pharmaceutical formulation for parenteral administration to a human, comprising:
   the pharmaceutical formulation of claim 1, admixed with pharmaceutically acceptable fluids.

7. A process for preparing a concentrated anhydrous melatonin solution, comprising the steps of:
   admixing a PED selected from the group consisting of macrogolglycerol hydroxystearate (polyoxyl 40 hydrogenated castor oil), with restriction of the nominal value to 40-45, and macrogol 15 hydroxystearate (polyoxyl 15 hydroxystearate), with nominal value 15, with an equal mass of either MLT or MLTEP in the optimal ratio of 1:1 (weight/weight) and thoroughly kneading;
   dissolving the admixed MLT-MLTEP/PED in 10 volumes of ethanol being the ratio MLT-MLTEP/PED/Ethanol 1:1:10 (weight/weight/volume), thoroughly mixing by vortex to yield a concentrated melatonin solution; and
   filtering the concentrated melatonin solution to meet the requirements of microbiological enumeration test for total aerobic microbial count ("TAMC") max 10-2 CFU/g and total combined yeasts and moulds count ("TYMC") max 10 CFU/g; and apportioning a fixed volume of the concentrated melatonin solution into a primary unit-dose or multi-dose container made from amber light-resistant pharmaceutical glass type 1, using nitrogen as a purge and process gas.

8. The pharmaceutical formulation of claim 1, wherein the melatonin solution has an endotoxins content of less than or equal to 300 IU/ml, a pH in the range of 6.5 to 7.5 and a moisture content of less than 4.0%.

9. A packaged unit-dose or multi-dose container of suitable volume holding from 0.5 to 20 ml of the concentrated melatonin pharmaceutical formulation of claim 1.

10. The pharmaceutical formulation for parenterally administering, in a sterile solution, an exact dose of melatonin to a human at an appropriate infusion speed during an extended period, comprising:
a predetermined volume of the sterile pharmaceutical formulation of claim 1; and
a compatible diluting fluid for injections as sodium chloride intravenous infusion, hypertonic saline of the designed strength without or with hydroxyethyl starch.

11. A composition of a pharmaceutical or a nutraceutical nature for enteral administration whenever a therapeutic effective dose of melatonin is required by oral administration, including prophylactic purposes as it may be directed, comprising: a precise volume of the pharmaceutical formulation of claim 1, diluted by an appropriate volume of purified water or of an aqueous solvent.

12. A unit-dose of the pharmaceutical formulation of claim 10, wherein the composition for parenteral use conveniently delivers from 0.01 mg/ml up to 10 mg/ml of melatonin, preferably from 0.1 mg/ml to 5.0 mg/ml, and from 0.1 mg to 1000 mg melatonin/dose unit as applicable, preferably from 0.5 mg to 100 mg.

13. The pharmaceutical formulation of claim 11 wherein the optimized enteral medicinal product or nutritional composition is characterized that diluent fluid is water for pharmaceutical use without any active ingredient or containing one or more active substances chemically compatible with melatonin.

14. A diluted solution of the pharmaceutical formulation according to claim 13, wherein the auxiliary excipients are selected from the group consisting of: glycerol (E422), xylitol (E967), neohesperidine DC (E959), sorbitol (E420), saccharin and its salts (E054).

15. The pharmaceutical formulation of claim 1, wherein the PED comprises polyoxyl 40 hydrogenated castor oil.

16. The pharmaceutical formulation of claim 1, wherein the PED comprises polyoxyl 35 castor oil.

17. The pharmaceutical formulation of claim 1, wherein the PED comprises polyoxyl 15 hydroxystearate.

18. A method for obtaining an overnight effective blood level of melatonin in the range of up to 70 to 85 ng/ml in a human subject, comprising the step of:
administering intravenously the diluted solution of claim 10 at a total dose of 100 mg during 5 hours (20 mg melatonin/hour).

19. A method for administering a therapeutically effective high dose regimen of intravenous melatonin to a human subject to prevent bleeding problems at the tissues and organs in critical health conditions due to Ebola hemorrhagic fever (EHF) and Dengue hemorrhagic fever (DHF) and other critical health conditions, comprising the step of:
administering the diluted solution of the pharmaceutical formulation of claim 12 to provide an adjuvant treatment.

20. A method of providing melatonin as a nutraceutical composition, comprising the step of:
adding the diluted solution of claim 13 to a food in the form of bulk solution.

21. A method for the prophylaxis or treatment of a human disease or condition, comprising the step of:
administering an effective amount of the pharmaceutical formulation of claim 10 to a subject in need of melatonin.

22. A pharmaceutical formulation according to claim 1, suitable for parenteral administration in humans to prevent bleeding problems at the tissues and organs in critical heath conditions due to Ebola hemorrhagic Fever (EHF), Dengue hemorrhagic fever (DHF) and neonatal hydrocephalus due to Zika.

* * * * *